US006938277B2

(12) United States Patent  (10) Patent No.: US 6,938,277 B2
Lindahl                    (45) Date of Patent:    Sep. 6, 2005

(54) REMOVABLE EYEWEAR MEMBER

(76) Inventor: Arthur Charles Lindahl, 242 Glen Ellen Dr., Ventura, CA (US) 93003

( * ) Notice: Subject to any disclaimer, the term of this patent is extended or adjusted under 35 U.S.C. 154(b) by 242 days.

(21) Appl. No.: 09/944,995

(22) Filed: Aug. 31, 2001

(65) Prior Publication Data

US 2002/0029408 A1 Mar. 14, 2002

Related U.S. Application Data

(63) Continuation-in-part of application No. 09/352,898, filed on Jul. 13, 1999, now Pat. No. 6,282,727.

(51) Int. Cl.[7] .................................................. A61F 9/02
(52) U.S. Cl. ................................ 2/434; 2/443; 351/158
(58) Field of Search ............................. 2/434, 426, 428, 2/430, 431, 439, 440, 441, 442, 443, 9, 12, 13; 351/47, 158, 155

(56) References Cited

U.S. PATENT DOCUMENTS

| | | |
|---|---|---|
| 1,853,872 A | 4/1932 | Myrowitz |
| 2,918,676 A | 12/1959 | Metheson |
| 3,133,982 A * | 5/1964 | Janz .......................... 2/426 X |
| 3,233,249 A | 2/1966 | Baratelli et al. |
| 3,233,250 A | 2/1966 | Johassen |
| 4,070,103 A | 1/1978 | Meeker |
| 4,176,410 A | 12/1979 | Matthias |
| 4,338,004 A * | 7/1982 | Vosper ......................... 351/47 |
| 4,405,212 A | 9/1983 | Cooper |
| 4,447,914 A | 5/1984 | Jannard |
| 4,515,448 A | 5/1985 | Tackles |
| 4,571,748 A | 2/1986 | Carroll et al. |
| 4,674,851 A | 6/1987 | Jannard |
| 4,730,915 A | 3/1988 | Jannard |
| 4,779,291 A | 10/1988 | Russell |
| 4,822,161 A | 4/1989 | Jimmy |
| 4,824,233 A | 4/1989 | Jannard |
| 4,859,048 A | 8/1989 | Jannard |
| 4,867,550 A | 9/1989 | Jannard |
| 4,868,930 A | 9/1989 | Blackstone |
| 4,934,807 A | 6/1990 | Bollé |
| 4,944,312 A | 7/1990 | Smith |
| 4,958,923 A | 9/1990 | Rosenson |
| 4,964,714 A | 10/1990 | Weymouth |
| 5,016,292 A | 5/1991 | Rademacher |
| 5,033,128 A | 7/1991 | Torres |
| 5,054,903 A | 10/1991 | Jannard et al. |
| 5,056,163 A | 10/1991 | Chou |
| 5,093,940 A | 3/1992 | Nishiyama |
| 5,098,180 A | 3/1992 | Tobey |
| 5,138,723 A | 8/1992 | Bollé |
| 5,191,364 A | 3/1993 | Kopfer |
| D339,364 S | 9/1993 | Bollé |
| D339,596 S | 9/1993 | Konfer |
| 5,243,711 A | 9/1993 | Graham |
| 5,339,119 A | 8/1994 | Gardner |
| 5,371,554 A | 12/1994 | Aspesi |
| 5,412,438 A | 5/1995 | Bollé |
| 5,428,411 A | 6/1995 | Kopfer |
| 5,617,588 A | 4/1997 | Canavan et al. |
| 5,894,606 A | 4/1999 | Chiang |
| 6,052,828 A | 4/2000 | Widdemer |
| 6,062,688 A | 5/2000 | Vinas |
| D428,913 S | 8/2000 | Kopfer |
| 6,094,751 A | 8/2000 | Parks |
| 6,139,144 A | 10/2000 | Hynansky |
| 6,149,268 A | 11/2000 | Hall et al. |
| 6,233,342 B1 | 5/2001 | Fernandez |
| 6,641,263 B2 * | 11/2003 | Olney .................... 351/158 X |

* cited by examiner

Primary Examiner—Peter Nerbun
(74) Attorney, Agent, or Firm—Curtis L. Harrington

(57) ABSTRACT

Eyewear member includes a structure for fitting peripherally on or around or behind lens and structure of conventional eyewear. Interfitting structure ranges from sealing segments to eyewear members which may attachably engage or simply interfit behind conventional eyewear. The eyewear members enables conventional eyewear to form a closer fit with the face of the user to protect the person's eyes from wind, water and foreign material. All embodiments contemplate selectable removabilty, replace ability and interchangeability.

4 Claims, 16 Drawing Sheets

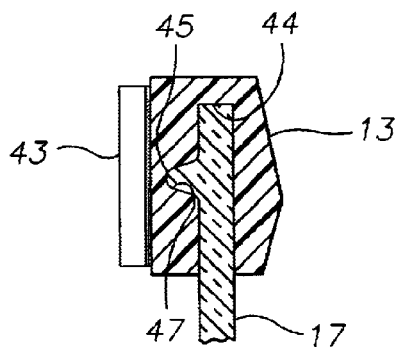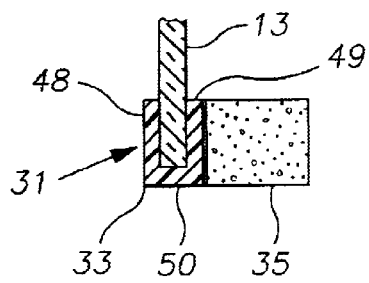
FIG. 3   FIG. 4
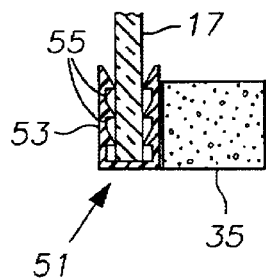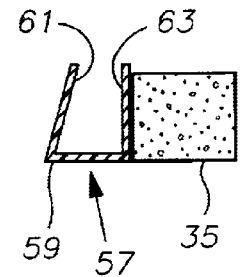
FIG. 5   FIG. 6
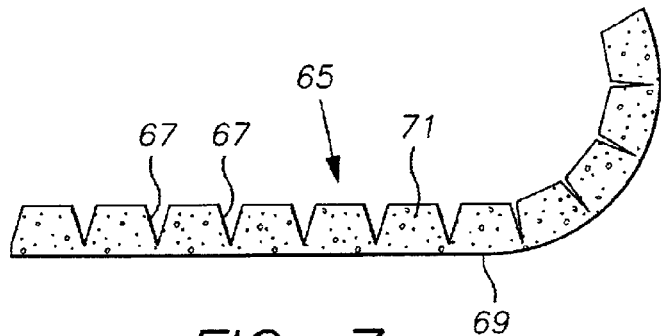
FIG. 7
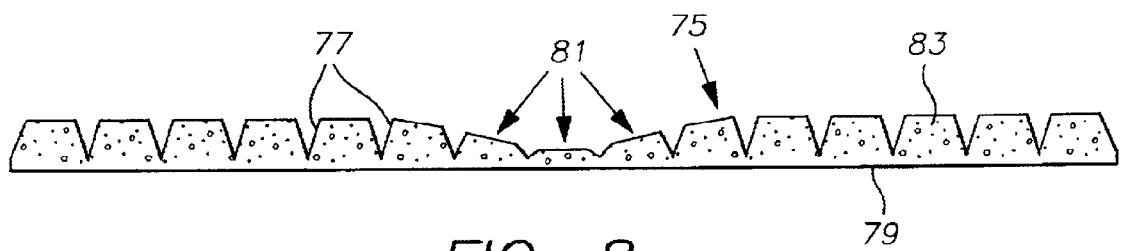
FIG. 8

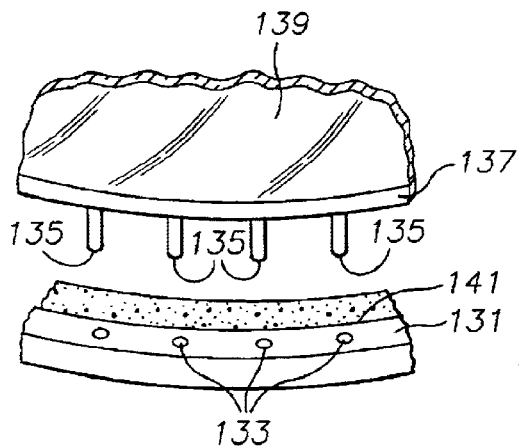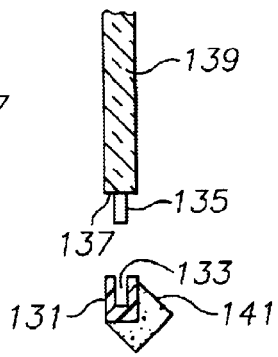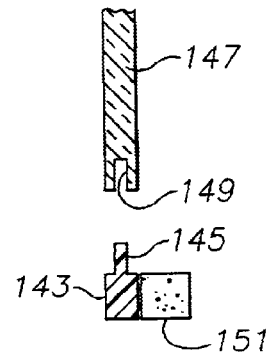
FIG. 17   FIG. 18   FIG. 19
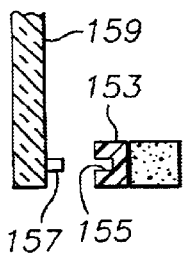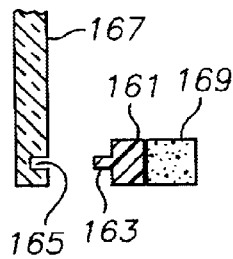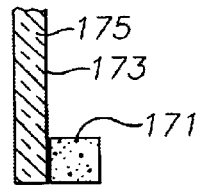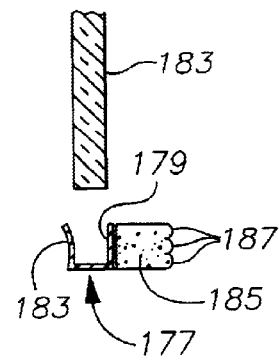
FIG. 20   FIG. 21   FIG. 22   FIG. 23
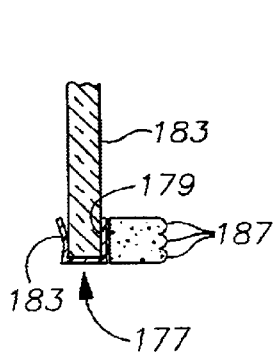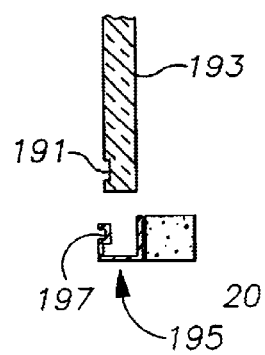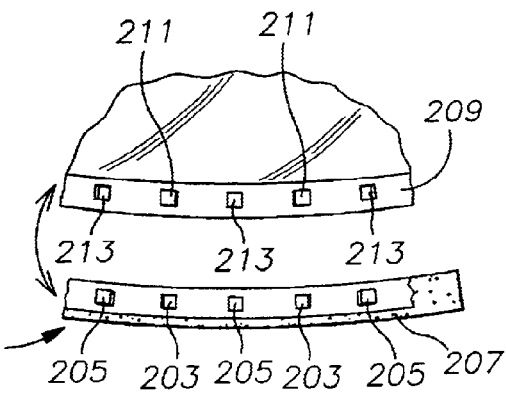
FIG. 24   FIG. 25   FIG. 26

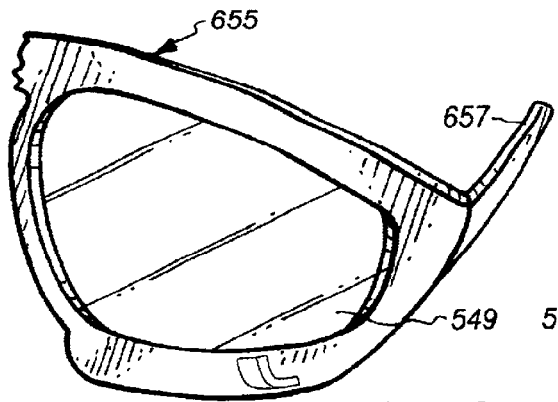
FIG. 58
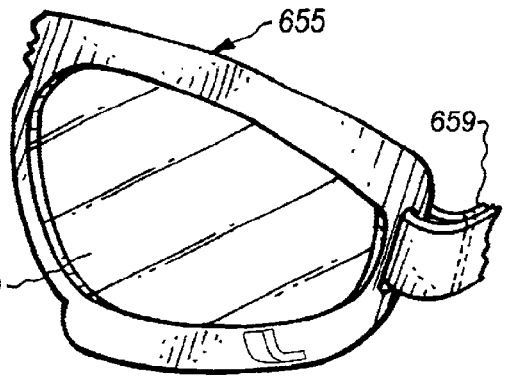
FIG. 59
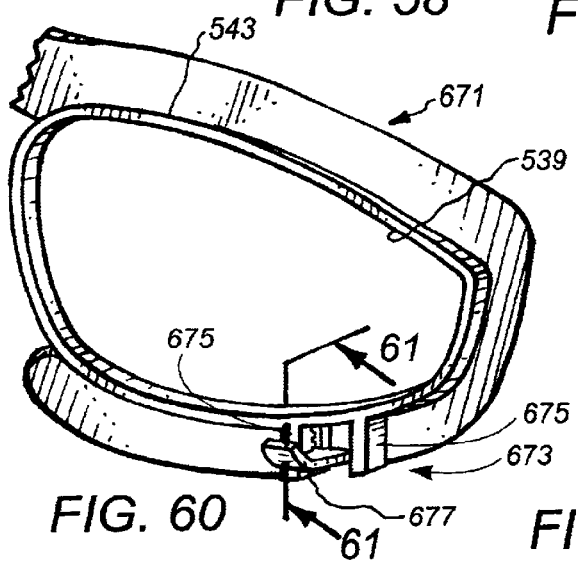
FIG. 60
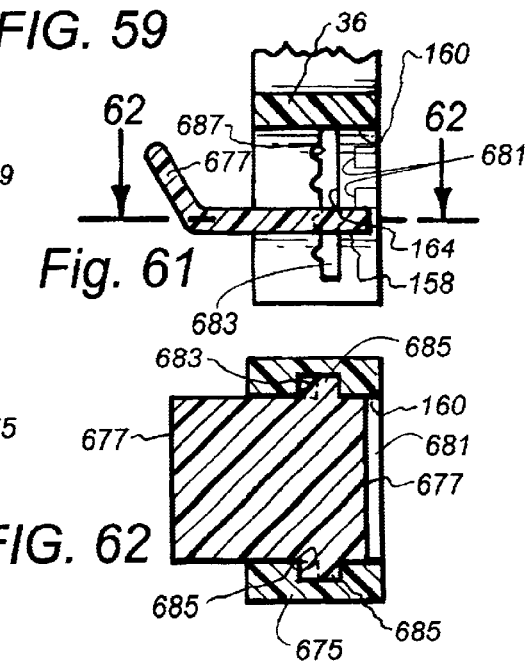
Fig. 61
FIG. 62
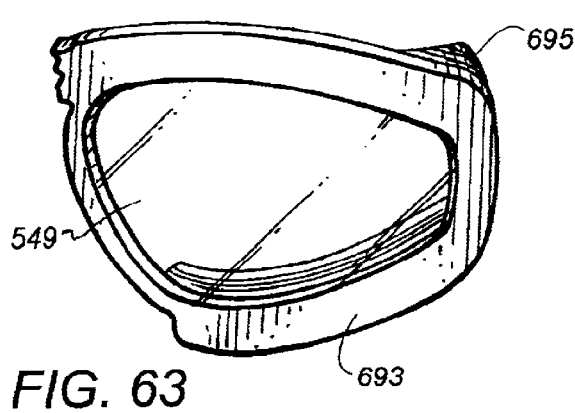
FIG. 63
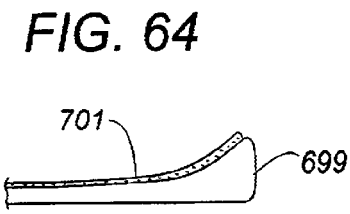
FIG. 64

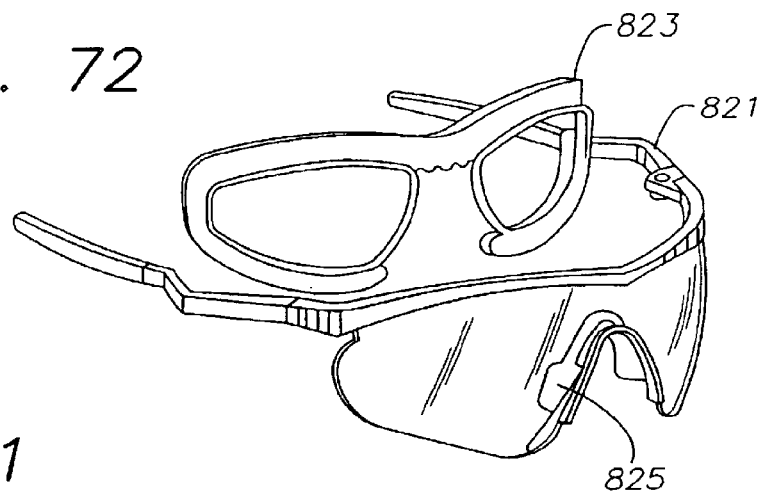
FIG. 72
FIG. 71
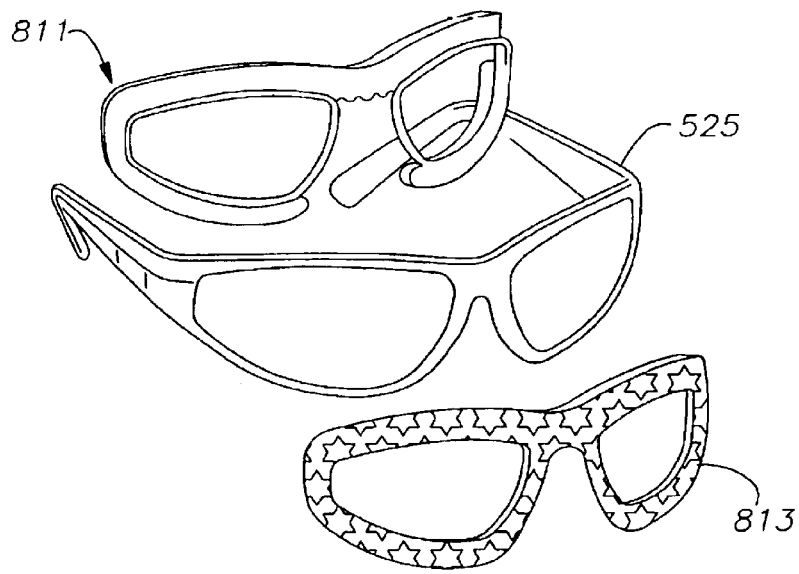
FIG. 74
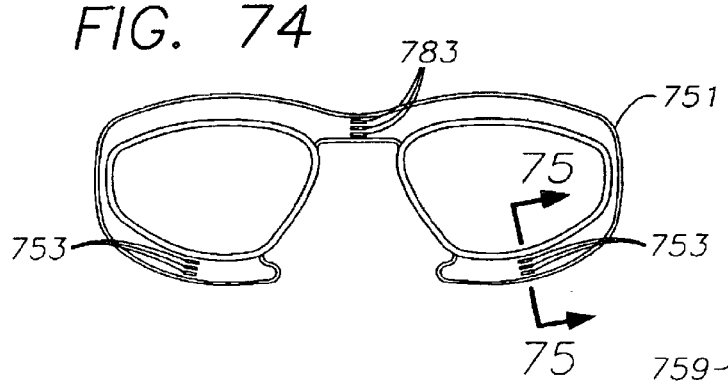
FIG. 75
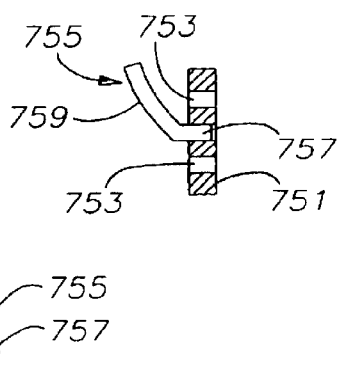

REMOVABLE EYEWEAR MEMBER

This application is a continuation-in-part of application Ser. No. 09/352,898, filed Jul. 13, 1999 now U.S. Pat. No. 6,282,772, by the present inventor, entitled SPORTS EYEWEAR WITH DETACHABLE GOGGLE MEMBERS.

FIELD OF THE INVENTION

The field of this invention relates to eyeglasses and sunglasses and more particularly to improved removable eyewear members for eyeglasses and sunglasses to broaden their usage so as to substantially deflect at least one of light, dust, liquid or debris from entering into the eye region which occurs through the gaps between the face and the eyeglass or sunglass, as an improved elemental deflecting system.

BACKGROUND OF THE INVENTION

Conventional sports & safety eyewear currently exist which allow the user a wide angle of view. This particular type of eyewear is typified by a singular or two lenses which extends from the outside of one of the wearer's eyes and extends across to the outside of the other of the wearer's eyes, and only partially interrupted by the structures which support the eyewear at the bridge of the nose. This is a partial interruption since the support structures are typically supported only by the center of the singular lens, which is in turn supported by the upper portion of the lens support structure. The support structure extends inside the singular lens to garner support from the user's nose, and the singular lens is kept outward and generally downward opening downward and lower on the user's face. Thus the wide view afforded by the singular lens comes at the expense of having a wide open space between the peripheral edge of the lens or lens support structure and the user's face. The same issues occur in two lens eyewear in the wide open space between the lens & user's face.

Goggles, which are different from conventional non-goggle eyewear, are considered to be extremely restrictive, as they typically hug and seal with the face of the user to isolate the eyes as much as possible from wind and debris, but they are typically used only in extreme conditions and not, for example to walk upon the beach or to play volleyball, two instances where a more relaxed, lightweight and non-constricting eyewear is the general preference. Also, sunglass use is limited for some people who require an extreme structure around the head for certain sports, or due to the fact that they have had laser surgery and require greater protection for their eyes. They could not effectively wear their normally extremely restrictive sports eyewear at all times without suffering a great deal of discomfort.

Extremely restrictive head wear can work well, but generally for only specific situations, such as riding a motorcycle or skiing. However, they fall short of being practical when used generally as a sunglass or spectacle, driving a car, or having lunch at an outdoor cafe. This is due to their being large, bulky, hot, and not very stylish for such activities. Attempts have been made to overcome the bulk and size of such extremely restrictive head wear by attempting to make fixed seal glasses, as are seen in Design Patent No. Des. 339,596. Although more stylish, these fixed seal sunglasses fall short of an ultimate solution for an all around eyewear product. This is because the user is left to using the hot, restrictive eyewear all the time due to the inability to attach and detach a sealing member at times when desired. The attempts to ventilate the lens support structures of these fixed seal, extremely restrictive sunglasses works adequately with high motion activities, but does not make them less hot at times when there is no air circulation going through the ventilating areas such as when driving in a car. Also, due to the rigid nature of eyewear lens support structures, and the many variances of the specific contour of the facial region surrounding the eyes of the user, certain users are left with a generally poor fit and incomplete sealing using a fixed seal with a given configuration, and which lacks customizability. Also upon breakdown of the sealing structure for a fixed seal extremely restrictive sunglasses, the user is left with the inability to easily replace their sealing structure, virtually eliminating the total benefits of the product they had purchased.

The sealing can occur around each eye, and the protected area most often includes the bridge of the nose. Even where the enclosure extends across the area adjacent both eyes, extremely restrictive eyewear can still generally restrict the view of the user. The restriction usually comes with the support structure which is used to seal against the face and closely adjacent to the eyes, and typically surrounds the entire lens fully. The term "conventional eyewear" includes eyeglasses, spectacles, sports eyewear and in general any eyewear which is not expected to provide a seal to the user's eye areas.

In terms of usage, a user is faced with having to buy both extremely restrictive eyewear and conventional sports glasses, and to use the appropriate eyewear depending upon circumstances. Where debris is severe enough, such extremely restrictive eyewear are worn at the sacrifice of an expanded viewing angle, more heavily structured and bulky. Where conventional open sports eyewear are worn, the user suffers the debris, particularly wind and dust, which may enter the eyes behind the lenses. In addition, conventional sports eyewear, by having a significant gap on the face, even where the gap between the bottom of the lens and the face surrounding the eyes is low on the face, admits significant amounts of light. Where the user gazes down, there will be a sudden change in light levels, which can both annoy the user and stress the user's eyes. The effect is most pronounced where the lens is particularly dark.

Another aspect of eyewear not served well by extremely restrictive eyewear includes the ability for comfort and ventilation. A good seal is usually achieved at the expense of ventilation and with significant pressure on the face surrounding the eyes. In some cases specialized ventilation ports are formed in the side walls of the lens support structures, but they are not always located properly or structured to provide adequate ventilation. Even where adequate ventilation is provided, the such extremely restrictive eyewear do not provide a comfortable fit.

Lack of comfortable fit is not an acceptable tradeoff for durability and long usage life. The seal used in conventional extremely restrictive eyewear is less able to withstand vigorous use, and tends to break down over a relatively short period of time. The seal break down usually occurs far short of the full use life. Therefore, the ability to interchange seals is important in extending the life of any eyewear, extremely restrictive or otherwise.

What is therefore needed is a new and improved sports eyewear structure such as may possibly be used with at least one lens member and having structures which may engage the lens member along the peripheral, separate or in conjunction with a top and/or side edges, or peripheral edges, adjacent surfaces and other surfaces and which will permit a very gentle sealing with the face to inhibit wind and debris from entering the user's eyes and which will block unwanted light from the eyes. Further, to benefit interchange ability, the structures which forms the seal which should be removable so that a wearer can use the same eyewear in an open or closed format as the user wishes.

Apart from the abovementioned sports eyewear which may have a huge opening, especially at the bottom of a user's eyes, there is also the problem generally found in conventional eyeglasses, spectacles, and many sunglasses inherently do not have a close fit with the user's face. It seems there is always a sizeable gap area, though varying in size, entirely surrounding the lens support structure of the eyeglasses. This gap area, at times, can be annoying and can even be dangerous and life threatening, and more than simply high speed sports activities, side gusts of wind are provided with an even easier entrance and exit. The annoyance can be due to the entry of wind, dust, water and light to the user's eyes. Wind and dust can be encountered anytime one is outdoors, in particular when dealing with high speed sports like skiing, motorcycling or power boating, especially where the head often assumes different angles to the direction of travel. The level of light to one's eyes can also be annoying. For example, when the sun is shining brightly and a user is playing golf, the sun can have a blinding affect making it difficult for the user to make a golf shot. Entry of water can also he annoying when engaged in some water sports, such as boating and kayaking. The gap area becomes dangerous, for example, when bodily fluids from a patient with a communicable disease in a medical situation comes into contact with the eyes of the medical practitioner. Entry of blood into the eyes from an aids patient could be life threatening.

There are many varieties of eyewear. For example, one specific type of eyewear is a lens support structure which forms a mounting for a pair of corrective vision lenses and this lens support structure is generally adapted to rest on the bridge of one's nose with the prescription corrective vision lenses being located directly in front of one's eyes. However, using of these type of eyewear structure is highly deficient in reducing particulates from entering the eye region, when adapted for use in a variety of industrial safety eyewear, eyewear for swimming, motorcycle riding, skiing and the like. A similar deficiency arises using most conventional sunglasses and eyewear which have temple members.

What is also needed are improvements in light weight eyewear members which enable the user to selectably convert a greater percentage of eyewear of known art into debris blocking eyewear or sun shields for times when needed. The conversion of the eyewear to a condition where it may block debris can also be selectably reversed by the user with the eyewear being changed back to its former state when debris blocking is not needed. It would be desirable if the eyewear member could be easily stored in a user's pocket or purse, preferably as a single integrated unit. It would also be desirable for the eyewear member unit to adapt to a wide range of different shapes and sizes of eyewear, so that a user could use one unit on several different styles and physical configurations of eyewear that the user may own. The eyewear member should be utilizable with conventional eyewear which does not inherently have the ability to seal out wind and debris, also known herein as conventional eyewear.

SUMMARY OF THE INVENTION

Conventional eyewear may include a single piece lens or two lenses which may or may not be supported and captured within a support structure. Possible lenses include removable lenses, anti-fog lenses, prescription lenses, as well as systems supplied as lens-only.

The lens or eyewear lens support structure may be engaged by a removable member having a sealing structure extending to one side. The side of the sealing structure extension which meets the face preferably has a smooth, non-porous surface to avoid collection of debris, body oil, although since the memner is removable and easily washable, an open cell foam or other porous material, as well as a completely closed foam, non-extenally porous material can be used as the sealing structure, would also be permissable. The sealing structure may operate in conjunction with a built-in or removable side shield and may accommodate a permanent or removable nosepiece.

The removable fitted member engages at least one of a peripheral edge, surface or adjacent surface of the lens or lenses or support structure for the lenses and may extend from a point near the outermost edge or adjacent the outermost edge of one side of the eyewear, or face and to the nose area. The end of the removable fitted member can be shaped to provide maximum accommodation of the nose support member and help seal in a manner complementary to the nose support member.

In another embodiment, the removable fitted member can extend from one side of the eyewear, completely through to the other side of the eyewear and form the structure which supports the lens against the nose. In both embodiments, the removable fitted member is intended to include the possibility of alteration by the user by cutting, trimming and the like to obtain maximum conformance to the particular shape of the user's eyewear.

The removable fitted member may include a support piece, which may be made from any suitable material including plastic, metal, and the like, and may have a generally U-shaped cross section for engaging the peripheral edge of the lens or structure supporting the lens, and a small angled channel, extending from the bottom portion of the U-shape which helps to support the sealing structure which seals against the face. Along the length of the channel, a series of elongate rectangular ports assist in handling the drainage of any sweat, or any rain or moisture which might have entered the eye shield area and collect along the bottom of the lens.

The support piece will typically be extruded or injected and may be heat formed to a specific shape where it is desired to provide eyewear as a kit. Where the removable fitted member is provided as a retro-fit device for use with non-specific shapes of lenses, the removable fitted member will ideally have a series of angled slots along its length to permit bending conformance to a wide variety of shapes of lens peripheral areas without twisting or distorting the material. In another embodiment, shorter sections of material may be fitted along the peripheral areas of lens members, including top, side, bottom edges and on the lens support members of the lens, and may be easily removable by the user. Member of any of the structures of the invention may be had by gluing, hooking or clipping, chemical bonding, welding, friction fit, screws, pressure, male and female pins and holes, member channel and groove, hook and loop members, magnets, suction, static attraction, melting or solvent, and independent member to other structures including any portion of the eyewear support structures, temples, strap or lens. The structures of the invention may include homogeneous structures, or structures made of two or more different types of material. Materials which can be used include wood, metal, plastic, leather, cloth/fabric, foam, rubber, conforming material and any other material capable of making the seal now known or later discovered. Manufacture of the structures of the invention can occur by extrusion, injection, shaping, forming, molding or other manufacturing steps now know or later discovered.

A further embodiment of the eyewear member is directed for use by a person wearing a single lens, also known as a shield type design, or two lens design (right and left separated lens, typically with a single or separated support). The two lens design includes conventional spectacle style eyewear. The eyewear member may comprise a substantially planar, thin walled support structure that has an enclosing body with at least one enlarged opening. The enlarged opening aligns with the position of the user's eyes in front of the eyewear lens or lenses. The eyewear member may provide a very close fit with the face of the person using the eyewear member to diminish the entry of foreign material and light between the eyewear and the person's face. The eyewear member includes a means for removing or securing the eyewear member to the eyewear.

A further embodiment is a design having two enlarged openings dividing the eyewear member into a pair of eyewear sections, for at least one of the advantages including more sealing and more supported engagement of the eyewear.

A further embodiment of the involves an overall design such that the two eyewear member sections are then being connected by a bridge.

A further embodiment of the design includes as a starting point the previous embodiment, with further modifications by having the bridge including structure for completely segregating and separating the individual eyewear member sections from each other.

An alternative of the previously described embodiment is had where the structure for completely segregating and separating the individual eyewear member sections from each other further includes a telescoping interconnection in order to provide enhanced adjustability. A further variation of this design is seen as a further embodiment in which the mechanism of separation further includes an interlocking structure. Another embodiment of the structures as described above involves a design where the mechanism for separation comprises a removable angular projection member. In another embodiment, the mechanism for separation further comprises a magnetic attraction member.

A further embodiment provides for easy removal and installation of an eyewear member support structure relative to the eyewear. A further embodiment is obtained by the use of at least one U-shaped or angled projection member connected to the detachable eyewear member with each angled projection member configured to engage the eyewear. In a further embodiment, at least one of the U-shaped members described are configured to be adjustable relative to the eyewear member and the eyewear it engages so as to achieve usage of the eyewear member on a greater number of different designs and shapes of eyewear. In yet another embodiment related to the Angled projection member, the Angled projection member is modified by being removable from the eyewear member altogether. This configuration allows the user to achieve usage of the eyewear member on a greater number of different designs and shapes of eyewear by inter-changing different shapes or lengths of the Angled projection member for maximum utilization.

A further embodiment is obtained where a nose piece securing mechanism is mounted on the eyewear member and connected to the nose bridge area of the eyewear, with the nosepiece securing mechanism being adapted to engage with the nose of a person wearing the eyewear member. A further embodiment utilizes a magnet affixed to the eyewear member which cooperates with the conventional eyewear to hold the eyewear member in place. In a variation of this embodiment, a further embodiment involves the production of the mechanism for securing by forming an eyewear member impregnated with magnetic matter.

Yet a further embodiment is seen where the mechanism for securing comprises angular projection members that are affixed to the eyewear member for engagement onto the eyewear, and another embodiment includes angular projection members that lock the eyewear member to the eyewear. In another embodiment is a mechanism for securing comprising spring-type angular projection members which connect to the eyewear member to secure the eyewear member to the eyewear. A further embodiment is for enabling the mechanism for attaching to be selectively removed from the eyewear member to further facilitate using different securing methods based upon the shape and design of the eyewear. A further embodiment includes a design where the mechanism for securing comprises a front and back eyewear attachment which sandwiches together around existing eyewear, with the front piece for creating a new look for the existing eyewear, and with the back piece acting as both a carrier for the front piece and as a sealing member. The front and back pieces can be attached to each other by either magnets, hook and loop, male to female parts or front and back spring hinged together on a peripheral edge to create a clam shell effect. Any attachment method will suffice, and it is desirable that a complementary system be utilized.

Where attachment to the front of conventional eyewear is desired, an embodiment may be provided to attach from the front of the eyewear, rather than the rear, with a seal that extends from the carrier, typically around the eyewear, to the surface of the wearers face. All previous methods of attachment can also be utilized with this embodiment.

A further embodiment is where one of the earlier embodiments is modified to include at least one sealing member attached to the eyewear member for obtaining a close fit with the person's face. Yet a further embodiment is obtained where sealing member comprises a substantially straight segment having a tapered configuration defining a thicker area or areas and a thinner or flatter area or areas, especially interfit with the gap between the eyewear and user's face which similarly varies depending upon position.

A further embodiment is formed where any of the previous embodiments are modified to include a sealing member comprised of at least one ring shaped segment attached to the eyewear member. A further embodiment is obtained where the previous embodiment is modified by a sealing member being made in a tapered configuration defining thicker areas and thinner or flatter areas at designated points around the ring.

A further embodiment is had where any other embodiment is modified to include a sealing member that is attached to the eyewear member on both the forward side and the rearward side of the eyewear member. A further embodiment is had where a seal is attached to the bottom only of the eyewear attachment. A further embodiment is derived where a seal is attached to the top only of the eyewear member. A further embodiment is had where a seal is attached to the peripheral areas of the eyewear member. A further embodiment of the present invention is had where a seal is removably attached to the peripheral areas of the eyewear member. A further embodiment of is had where the seal is rigid and another where the seal is semi-rigid.

Yet further embodiments is formed where a previous embodiment is modified by the seal is removeably attached to the eyewear member utilizing substantially different sizes of seals according to individual desires and needs of a user. Another embodiment is formed where extra material is added to the eyewear member to "lift" the eyewear member away from the eyewear (and toward the user's face) to create a closer fit of the eyewear member to the user's face. Such "lifting" material can be added to the front or rear of the eyewear member, or both front and back.

A further embodiment can be obtained where the seal is being attached to a removable seal carrier having a uniform thickness which is then attached to the eyewear member. A further embodiment is derived where the seal carrier is modified to having a tapered configuration defining thicker areas and thinner or flatter areas at designated points. Another is where the seal carrier is modified to having telescopic abilities, when compressed being flatter, when opened having a tapered configuration defining thicker areas and thinner or flatter areas at designated points. Another embodiment is where the seal carrier is modified to having a slotted channel integrated in it to facilitate drainage of moisture. A further embodiment of the eyewear member is obtained by including a channel integrated in the attachment to facilitate drainage of moisture.

A further embodiment is obtained where any embodiment is modified by the enlarged opening, including corrective spectacle lenses, and with or without a modification of the eyewear member having mounted thereon a mounting mechanism for mounting of the eyewear member on the head of a user and where the mounting mechanism may or may not include a strap. A further embodiment is formed where any embodiment is modified by the enlarged opening of an eyewear member which includes plano lenses for changing the tinting of the eyewear to which it is attached. A further embodiment of the just previous embodiment is had by modifying an eyewear member having mounted thereon a mounting mechanism for mounting of the eyewear member on the head of a user, and whether or not the mechanism includes a strap.

Yet a further embodiment is obtained by modifying the enlarged openings of eyewear to include a thin sheet of optically correct material treated to reduce moisture collection within the confines of the eyewear member and the eyewear. A further embodiment includes a configuration where any embodiment is modified by eyewear member attachment being solidly molded such that the enlarged opening of eyewear is enclosed with transparent optically correct material for changing the tinting of the eyewear to which it is attached. A further embodiment includes a possible variation that an adjustment mechanism can be provided for varying the size of the enlarged opening.

A further embodiment is formed by providing an eyewear sealing system for removable deployment onto conventional eyewear having a peripheral region corresponding to a user's facial region surrounding the user's two eyes. The eyewear sealing system may comprise a resilient sealing member made and arranged to conform to a portion of the user's face and to extend from the eyewear for sealing out wind, debris and foreign matter. The eyewear sealing system may includes attachment means for mounting the resilient sealing member onto the eyewear in order to enable easy removal from the eyewear. The attachment mechanism may comprises a U-shaped channel mounted between a resilient sealing member and the eyewear.

BRIEF DESCRIPTION OF THE DRAWINGS

The invention, its configuration, and its construction will be further depicted in, and not limited to, the following detailed description, taken in conjunction with the accompanying drawings in which:

FIG. 3 is a view taken along line 3—3 of FIG. 1 and illustrating the manner in which the lens is held within the support structure with a projection extending perpendicular to the general planar surface of the lens and where the sealing member is removably attached;

FIG. 4 is a sectional view taken through a removable fitted member shown in FIG. 2 and illustrating the press fit member supporting the sealing member;

FIG. 5 is a variation on the removable fitted member of FIG. 4 and having a series of inwardly disposed engagement members;

FIG. 6 is a variation on the removable fitted member of FIGS. 4 and 5 which is extruded and pre-stressed to better engage the eyewear;

FIG. 7 is an example of a length of fitted material having a series of slots to enable easy conformance of the fitted material to the edge eyewear lens and its support structure and having any shape;

FIG. 8 is a continuous length of fitted material having a series of slots and cut in the middle to facilitate interfitting with a lens and lens support structure of an eyewear structure and for forming the nose bridge portion below the lens;

FIG. 17 is a perspective view of a bottom fitting protrusion member having a series of bores for interfitting with a series of downwardly extending pegs from the lower periphery of a lens or lens support and illustrating a rearwardly extending foam sealing member;

FIG. 18 is a side sectional view of the structure in FIG. 17, and illustrating the protrusion member's blind bores and which is attached to the bottom and rear surfaces of a bottom fitting protrusion member and having a main sealing surface at an angle to both bottom and rear surfaces;

FIG. 19 is a side sectional view of a variant of the structure of FIGS. 17 and 18, but where the protrusion member supports the series of pegs seen in FIGS. 18 and 17 and where the bottom surface of a lens or lens support includes a series of interfitting blind bores;

FIG. 20 is a side sectional view of a rearwardly fitting protrusion member having a series of forwardly directed bores for interfitting with a series of rearwardly extending pegs from the rearward surface of a lens or lens support and illustrating a rearwardly extending foam sealing member;

FIG. 21 is a side sectional view of a rearwardly fitting protrusion member having a series of forwardly directed pegs for interfitting with a series of rearwardly extending bores from the rearward surface of a lens or lens support and illustrating a rearwardly extending foam sealing member;

FIG. 22 is a side sectional view of a rearwardly fitting sealing member attached to the rearward surface of a lens or lens support utilizing at least one of glue, static plastic member or adhesive;

FIG. 23 is a side sectional view of a bottom fitting protrusion member in the shape of a channel having a "U" cross sectional shape upwardly disposed to fit around a lens or lens support structure and illustrating a rearwardly extending sealing member with a ribbed surface to insure greater sealing;

FIG. 24 is a side sectional view of a bottom fitting protrusion member in the shape of a channel having a "U" cross sectional shape and located in select areas around the lens or lens support, not continuously and shown in position on the bottom portion of a lens or lens support;

FIG. 25 is a variation on the side sectional view seen in FIG. 24 and in which at least a portion of a channel in the lower forward portion of a lens or lens support is engaged by one side of a clip-shaped or "U" shaped channel member having an extension of one side of the channel member into the channel to form a positive lock;

FIG. 26 is a perspective view of separated members of a rearward fitting protrusion member having a an alternating series of rectangular extensions and rectangular depressions, and having a rearwardly extending sealing member, and shown opposite the bottom rear surface of a lens or lens support and having a complementary alternating series of rectangular extensions and rectangular depressions, for interfitting with the rectangular extensions and rectangular depressions of the protrusion member for an interlocking fit;

FIG. 58 is an perspective view of a left eye section of a further embodiment of eyewear member of the present invention where the eyewear member can include temple earpieces for mounting of the attachment onto the head of the user;

FIG. 59 is an perspective view of a left eye section a further embodiment of eyewear member of the present invention where instead of temple earpieces there is utilized a strap to mount the eyewear member onto the head of a user;

FIG. 60 is an perspective view of a left eye section of a twelfth embodiment of eyewear member of the present invention which shows an adjustable Angled projection member;

FIG. 61 is a cross-sectional view of a spectacle attachment of the present invention taken along line 61—61 of FIG. 60;

FIG. 62 is a cross-sectional view of eyewear member of the present invention taken along line 62—62 of FIG. 61;

FIG. 63 is an perspective view of a right eye section of a thirteenth embodiment of eyewear member of the present invention;

FIG. 64 is a top view of an alternative construction of an eyewear member illustrating a built in lifter function along with a thin layer of sealing material;

FIG. 71 shows a clam shell arrangement wherein a magnetic eyewear member fits behind a conventional eyewear, and either by reach around or magnetic connection supports an decorative facade;

FIG. 72 illustrates an eyewear member seen in FIG. 69, but without angled projection member attachments and utilized on conjunction with a uni-lens conventional sports eyewear structure having a nose piece support;

FIG. 74 is a view of an eyewear member having a series of bores for fitting a bayonette style removable angular projection member; and FIG. 75 is a side sectional view taken along line 75—75 of FIG. 74.

DETAILED DESCRIPTION OF THE PREFERRED EMBODIMENT

Figure 1:
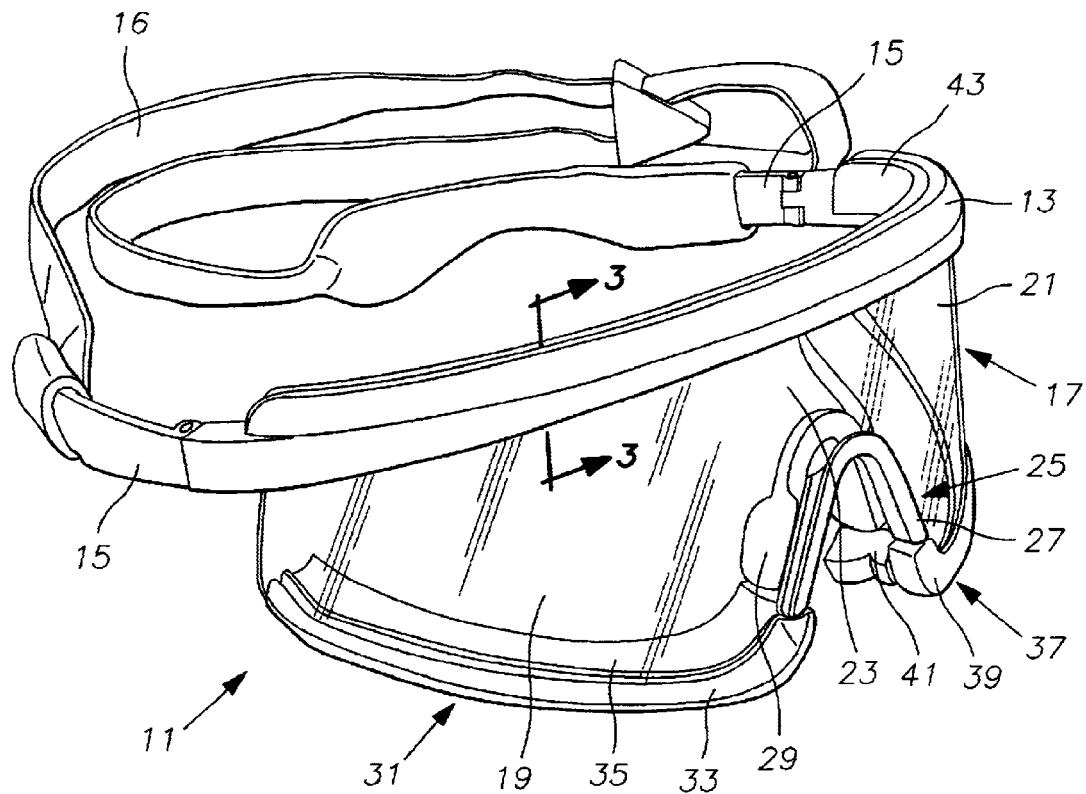
FIG. 1 is an illustration of a perspective view of the eyewear of the present invention and illustrating the removable fitted member attached as two pieces to the edge of a single lens and up to each side of the nose support structure and one removable fitted member attached to the upper lens support structure.

The invention will be best described with reference to FIG. 1 which illustrates a perspective view of sports eyewear 11. Eyewear 11 includes a curved frontal support 13, a pair of folding side temple supports 15 and which may be pivotally hinged to the frontal support 13. Here, a support strap 16 is shown engaging the ends of the temple supports 15.

Supported solely from the frontal support 13, a continuous lens 17 is suspended from the frontal support 13. The lens 17 has a right area 19 and a left area 21 separated by a nose area 23. The nose area 23 is the smallest vertical extent of the lens 17 and demarks some separation between the right and left areas 19 and 21 respectively. At and below the nose area 23 is a nose bridge support 25 which is attached to the lens 17. The nose bridge support 25 has a forward lens engaging portion 27 and a rearwardly extending nose bridge engagement portion 29. The support 25 is typically held in place by notches or other holding structure in the lens 17 which hold the support 25 in place.

Immediately below the right area 19 is a removable fitted member 31 having a fitted engagement piece 33 and a rearwardly extending sealing structure 35. The engagement piece 33 is typically made of a medium soft resilient plastic which can be slipped onto the bottom of the lens 17. A second removable fitted member 37 includes an engagement piece 39 and a sealing structure 41.

Engagement piece 33 follows the contour of the bottom edge (not seen where engaged) of the right area 19 of the lens 17. Here, the engagement piece 33 covers all of the bottom edge of the right area 19 and stops where the outer edge of the right area turns upward. The extent of engagement piece 33 need not stop here, but can continue upward if desired. At the rear of the curved frontal support 13, a continuous removable length of brow padding 43 may be provided. In such a configuration, the eyewear 11 is supported by a combination of the hugging action of the temple supports, the pressure of the frontal support 13 and brow padding against the forehead.

If the removable fitted member 31 were to extend up the vertical edge of the lens 17 of the right area 19, an enclosed volume surrounding the eyes results. The integrity of the enclosed volume is not as complete as would be the case for a full set of extremely restrictive eyewear, especially as would isolate the human head completely, but air movement, and thus movement of debris in the air stream is restricted.

In the configuration of FIG. 1, the engagement piece 33 will typically be purchased as a pre-fit to conform to right areas 19 having a generalized bottom edge configuration as shown in FIG. 1. It is possible that the engagement piece 33 could fit a number of configurations which are different, but which do not extremely deviate from the general shape seen in FIG. 1, or a similar general shape.

As can also be seen in FIG. 1, the sealing structure 35 extends up to and may have sealing contact with the rearwardly extending nose bridge engagement portion 29. The sealing structure 35 may thereby extend beyond the extent of the end of the fitted engagement piece 33 as it approaches the nose bridge support 25. The fitted engagement piece 33 may also abut the nose bridge support 25 and particularly the forward lens engaging portion 27.

Figure 2:
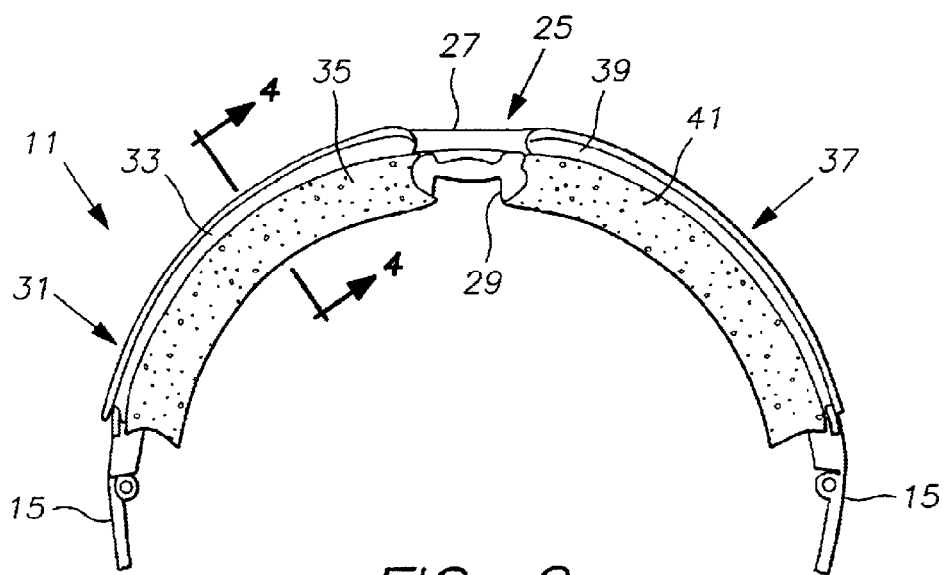
FIG. 2 is a bottom view of the eyewear of FIG. 1 and illustrating the prominence from a vertical angle of the sealing structure supported by the removable fitted members.

Referring to FIG. 2, a bottom view of the eyewear 11 of FIG. 1 illustrates the rearward extent of the sealing structures 35 and 41. A more complete view of the relationship of the forward lens engaging portion 27 and rearwardly extending nose bridge engagement portion 29 of the nose bridge support 25 is seen.

Referring to FIG. 3, an expanded view taken along line 3—3 of FIG. 1 is illustrated. The frontal support 13 has a slot 44 into which the lens 17 fits. The lens 17 has a rearward protrusion member 45 which rises significantly away from the planar extent of lens 17 and which interfits with a matching void 47 and both of which operate to keep the lens 17 secure within the curved frontal support 13. The overall shape of the member 45 may be round, square or triangular in both side and surface profile, and further configurations will be shown. The frontal support 13 is seen as having a downwardly directed slot 44, indicated by a lead line to the closed end of the slot, into which lens 17 fits.

Referring to FIG. 4, a generalized view of the fitted engagement piece 33 and attached sealing structure 35 is seen. The sealing structure 35 may be relatively long, both to give an adequate reach to the portion of the user's face being engaged, and to provide a softer fit by providing additional material for compression. The vertical depth of the material of the sealing structure 35 is sufficient to prevent any sagging or undue bending in a vertical direction. The fitted engagement piece 33 is seen as having a front wall 48 and a rear wall 49 both supported by a base member 50.

Referring to FIG. 5, a variation on the design of the fitted engagement piece 33 of FIG. 4 is shown as a fitted engagement member 51 having a fitted engagement piece 53 having internally disposed gripping members 55. Gripping members help to provide greater holding force by making it easier to mount the engagement piece 53 onto the lens 17 than the force required to remove it.

Referring to FIG. 6, a variation on the design of the fitted engagement piece 33 of FIG. 4 is shown as a fitted engagement member 57 having a fitted engagement piece 59 having inwardly tilting preformed side walls 61 to assist in gripping the lower edge of the lens 17 (not shown in FIG. 6 in order to show the degree of pre stress on at least one of the side walls 61). The inwardly tilting front and rear walls 61 and 63 help to better distribute the bearing force of the side walls 61 on the lens 17 material to prevent a loosening of the side walls from becoming worn and flared thus preventing good fit of the engagement piece 33.

Referring to FIG. 7, a continuous length of removable fitted member 65 has a series of generally evenly spaced notches 67 in its fitted engagement piece 69. The notches 67 are formed in both the front and rear walls, although only a front wall 71 is visible from the vantage of FIG. 7. The sealing structure 35 extends away from the viewer of FIG. 7, and where the sealing structure 35 is of sufficient height, as will usually be the case, the notches 67 will also extend into its material. The notches 67 are of sufficient depth to enable any length of the engagement piece to bend sufficiently to closely engage the lower edge of the lens 13 at its smallest curvature. In some cases where the sharpest and most gentle curvature spacing is known, the notches 67 will have different depth or different angularity. Areas of slight curvature will have sharply angled notches while areas of sharp curvature will have large angled notches.

The removable fitted member 65 may be available in a continuous length to enable the user to cut a length to cover as much of the lower edge of a lens 17 as is desired. In addition to cutting the length to suit, the ends can be angle cut to enable the sealing structure 35 to extend beyond the end of the engagement piece 69, or to allow the engagement piece 69 to extend beyond the end of the sealing structure 35. In addition, the sealing structure 35 and the engagement piece 69 may be cut in other configurations as are necessary to more closely conform to and accommodate structures on the eyewear 11.

Referring to FIG. 8, in some cases, an eyewear 11 structure may lack a nose bridge support 25. In this case, a removable fitted member 75 may be provided having notches 77 in an engagement piece 79 which also has a wide gently sloping notch 81 removed from both a front wall 83 and a rear wall (not shown) and associated portions of the sealing structure (also not shown). The gently sloping notch 81 or curved removal of material from the removable fitted member 75 will prevent visual obstruction near the nose area 23. Otherwise, the individual portions between the notches 77 would fan out about the upper curvature of the bottom edge of lens 17 in the vicinity of the upper end of the nose bridge support 25, causing the visual obstruction.

As was the case for removable fitted member 65, the removable fitted member 75 can be manufactured with a central gently sloping notch 81, and overly long lengths to either side of the notch 81. The user can position the notch 81 at the nose area 23, begin fitting the lengths adjacent to the notch 81 and then trim the outer ends of the removable fitted member 75 to fit the outermost edges of the lens 17 as are needed.

Figure 9:
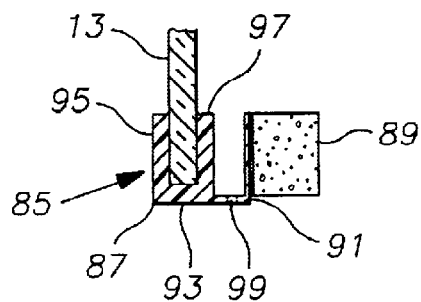
FIG. 9 illustrates a variation in the shape of the removable fitted member of FIG. 4 in which includes a small channel for support of the sealing member.

Referring to FIG. 9, a modification of the removable fitted member 31 is seen as a removable fitted member 85 having a fitted engagement piece 87 and a sealing structure 89 which may have a slightly shorter depth to accommodate a channel member 91. The channel member 91 is parallel to a base member 93 which supports a front wall 95 and a rear wall 97. The channel member 91 provides partial support for the sealing structure 89 and carries a series of drainage/ventilation slots 99 to help eliminate any moisture build up within the eyewear 11, and which moisture may be in gaseous or liquid form. If the sealing a structure 89 is sufficiently porous to air, the moisture in the air may exit through both the slots 99 and any other surface of the sealing structure 89 exposed externally. In the case of liquid droplets which may move down the inside of the lens 13, the slots 99 provide an exit at a point closest to the rear of the rear wall 97, for the liquid to escape.

Figure 10:
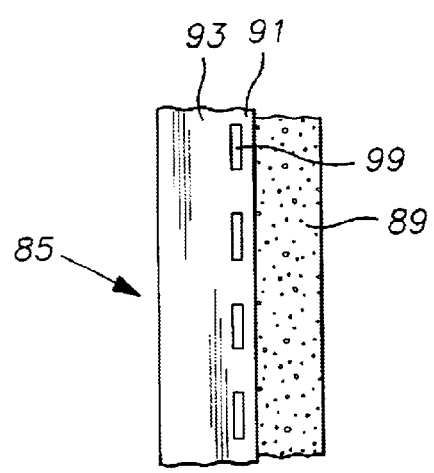
FIG. 10 is a bottom view of the fitted combination of FIG. 9 and illustrating a series of drainage slots formed in the small channel.
Figure 11:
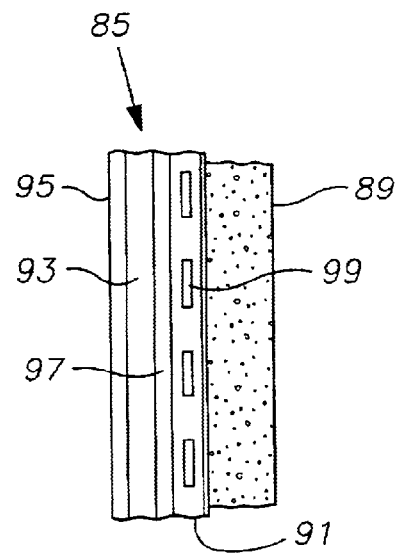
FIG. 11 is a top view of the fitted combination of FIG. 10 and illustrating a series of drainage slots formed in the small channel shown in phantom.

FIG. 10 is a bottom view of the removable fitted member 85 and illustrating the regularity of spacing of the slots 99, and the extent to which the sealing structure 89 extends beyond the edge of the channel 91. FIG. 11 is a top view of the removable fitted member 85 and showing the relationship of the front wall 95, rear wall 97 and base member 93. Also seen is the extent to which the sealing structure 89 both overhangs and is supported by the channel 91.

Figure 12:
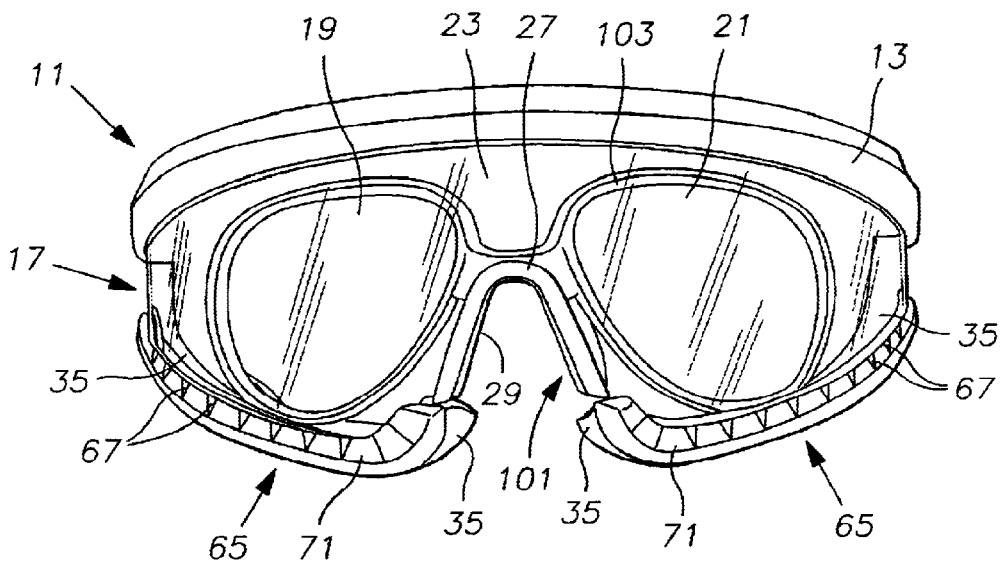
FIG. 12 illustrates a front view of an eyewear structure utilizing the removable fitted member of FIG. 7.

Referring to FIG. 12, the eyewear 11 is shown where the nose bridge support 25 is replaced by a nose bridge support 101 having an eyeglass support structure 103 supported by the rearwardly extending nose bridge engagement portion 29. With the combination shown in FIG. 12, the eyewear 11 provides an expanded view, double protection for the eyes and yet has an enclosure. Also seen are the removable fitted members 71 of FIG. 7 and the eyewear 11 is seen from a frontal angle of view. The continuousness the sealing structure 35 with respect to the rearwardly extending nose bridge engagement portion 29 is also seen. The sealing structure 35 can be seen through the lens 17 as rising all the way up to the level of the curved frontal support 13.

Figure 13:
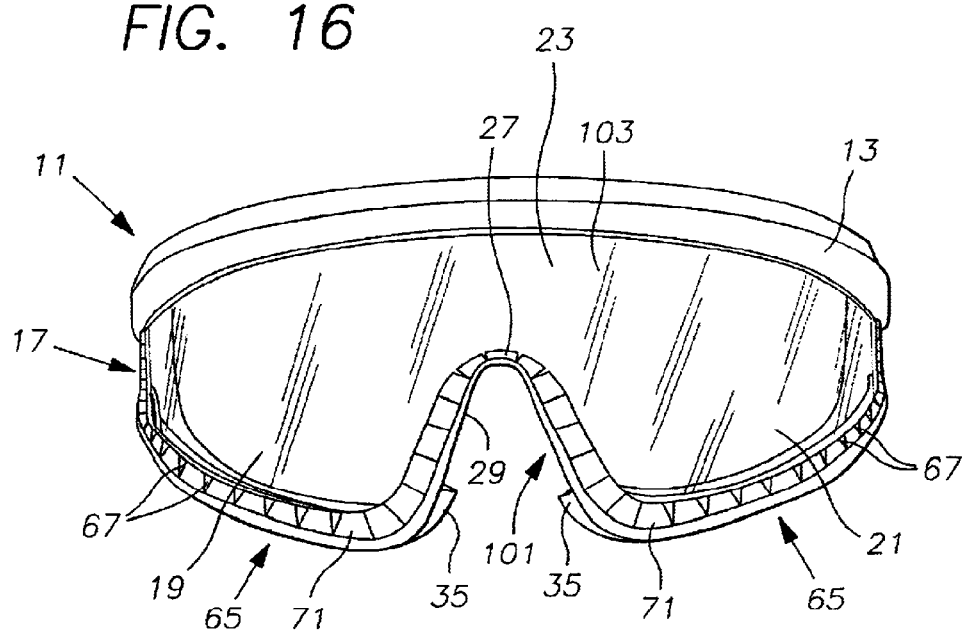
FIG. 13 illustrates a front view of an eyewear structure utilizing the removable fitted member of FIG. 8.

Referring to FIG. 13, the eyewear 11 is shown where the nose bridge support 25 and eyeglass support structure 103 is absent and where the removable fitted member 75 of FIG. 8 is shown extending completely around the edges of the lens 17 which are not engaged by the slot 44 of the frontal support 13. The removable fitted member 65 extends downward from the frontal support and takes a sharp curve naturally before extending toward the center of the eyewear 11 underneath right area 19, curving upward again and also taking advantage of the notches 77 and up to that point having always curved in a direction compressing the space occupied by the notches 77. At the bottom of the nose area 23, the removable fitted member 65 curves in the opposite direction as it goes over an area which will fit over the bridge of the nose. Here the wide gently sloping notch 81 comes into use by preventing the portions of the removable fitted member 75 between the notches 77 from flaring widely at the base of the nose area 23. This prevents obstruction of vision. The sealing member 35 is seen through the lens 17 and illustrated is the sealing member 35's extension up to the level of the curved frontal support 13. A portion of the sealing member 35 can be seen at the front center of the eyewear 11 and below the nose area. The sealing member 35 thus acts not only to seal the eyewear 11 against a wearer's face, but also to cushion the eyewear 11 against the bridge of the wearer's nose.

Figure 14:
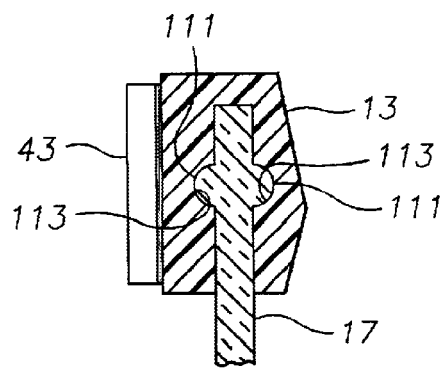
FIG. 14 shows an alternative method of engagement of the frontal support as was shown in FIG. 3, with the lens by using one or two oppositely disposed hemispherical protrusion members.

Referring to FIG. 14, a sectional view also taken along line 3—3 of FIG. 1 illustrates a variation on the rearward protrusion member 45 as a forward extending and rearward extending hemispherical protrusion member 111. It is hemispherical, with the radius lying on the general plane of the surface of the lens 19. The protrusion member 111 can be either in the forward position, rearward position or both. The illustration of FIG. 14 shows both forward and rearward structures for completeness. Each of the members 111 shown fit within a matching shaped hemispherical void 113 which lies off to one side of the slot 44 of the frontal support 13.

Figure 15:
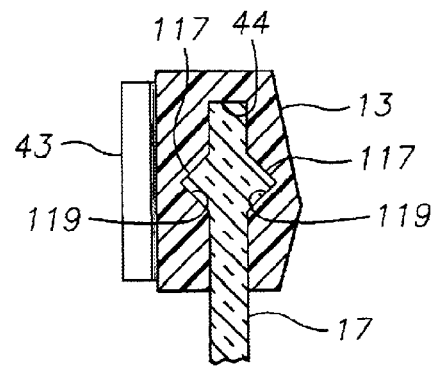
FIG. 15 shows an alternative method of engagement of the frontal support as in FIG. 14, where the protrusion members have an equilateral triangular shape.

Referring to FIG. 15, a sectional view also taken along line 3—3 of FIG. 1 illustrates a variation in shape of the forward extending and rearward extending hemispherical protrusion member 111, as a forward and rearward extending equilateral triangular protrusion member 117. The base of the triangular protrusion member 117 is about the same dimension as its two sides. The protrusion member 117 can also be either in the forward position, rearward position or both and is shown as both for illustration. Each of the members 117 shown fit within a matching shaped equilateral triangular void 119 which lies off to one side of the slot 44 of the frontal support 13.

Figure 16:
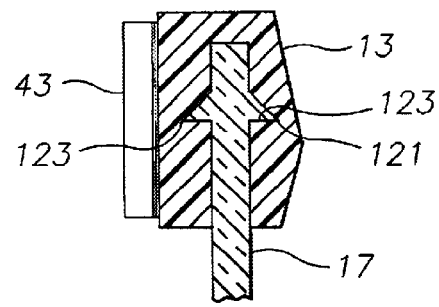
FIG. 16 shows an alternative method of engagement of the frontal support as in FIG. 15, where the protrusion members have a right triangular shape and are oriented to lock and capture the lens withing the frontal support in one direction.

Referring to FIG. 16, a sectional view also taken along line 3—3 of FIG. 1 illustrates a variation on the rearward protrusion member 45 as a forward extending and rearward extending right triangular member 121. The right triangular member 121 is oriented to facilitate the introduction of the lens 17 into the slot 44 and for a matching void 123 to capture the triangular member 121 within the void 123 to, in a less reversible way, capture the lens 17 within the slot 44. Depending upon the materials used, the difficulty in removing the lens 17 from the slot 44 will vary. The use of the member 121 will permit a lesser size member 121 to be used to give the same holding strength as another structure with a more reversible shape.

Beginning with FIG. 17, a further series variant structures for the invention are shown to illustrate the wide variety of structures and attachments which enable a sealing member to be secured relatively to a lens, such as lens 17, or a lens support structure surrounding an individually supported lens as is typically found in conventional eyewear. FIG. 17 is a perspective view of a bottom fitting protrusion member 131 having a series of bores 133 for interfitting with a series of downwardly extending pegs 135 from the bottom surface 137 of a lens 139. A rearwardly extending sealing member 141 is also seen. The pegs 135 fit into the bores 133 for a secure fit.

FIG. 18 is a side sectional view of the structure in FIG. 17, where protrusion member 131 blind bores 133 are shown in section. However, FIG. 18 shows a variation as a sealing member 145 which is mounted at an approximate 45° angle and in which a sealing member 141 has an upper surface for engaging a bottom of the protrusion member 131, as well as forward surface for engaging a rear of the protrusion member 131.

FIG. 19 is a side sectional view of a variant of the structure of FIGS. 17 and 18, but where a protrusion member 143 supports a series of pegs 146 and where the bottom surface of a lens 147 includes a series of blind bores 149 and where a sealing member 151 extends rearwardly of the protrusion member 143.

Referring to FIG. 20, a side sectional view of a rearwardly fitting protrusion member 153 having a series of forwardly directed bores 155 for interfitting with a series of rearwardly extending pegs 157 from the rearward surface of a lens 159. Affixation in any of the pegs, including pegs 157 into the bores, including bores 155 may be augmented by friction interference shape interaction, adhesive or glue or a snapping interfitting action.

Referring to FIG. 21, a side sectional view of a rearwardly fitting protrusion member 161 having a series of forwardly directed pegs 163 for interfitting with a series of rearwardly extending bores 165 from the rearward surface of a lens 167, is seen. Also seen is a rearwardly extending sealing member 169 having a rectangular profile.

Referring to FIG. 22, is a side sectional view of a rearwardly fitting sealing member 171 attached to the rearward surface 173 of a lens 175 utilizes at least one of glue, static plastic member or adhesive.

Referring to FIG. 23, a side sectional view of a bottom fitting protrusion member 177 is in the shape of a channel having a "U" cross sectional shape and has a rear wall which is opposite forward curved wall 181, the curvature to facilitate the upwardly disposed fitting onto a lens 183. A rearwardly extending sealing member 185 with a ribbed surface 187 to insure greater sealing. FIG. 24 is a side sectional view of the bottom fitting protrusion member 177 as seen in FIG. 23 and shown in position on the bottom portion of lens 183.

FIG. 25 is a variation on the side sectional view seen in FIG. 24 and in which at least a portion of a forwardly "U" shaped channel 191 is cut in a lower forward portion of a lens 193. A clip-shaped or "U" shaped channel protrusion member 195 has an extension of one side 197 of the protrusion member 195 into the channel 191 of the lens 193 to form a positive lock. When the protrusion member 195 is not in place with respect to the lens 193, an attractive channel 191 is seen. The depth, shape and detail relief of the channel 191 may be varied for decorative effect.

Referring to FIG. 26, a perspective view of a separated rearward fitting protrusion member 201 having a an alternating series of raised extensions 203 and depressions 205, and having a rearwardly extending sealing member 207, and shown opposite the bottom rear surface 209 of a lens support and having a complementary alternating series of raised extensions 211 and depressions 213, for interfitting with the raised extensions 203 and depressions 205 of the protrusion member 201 for an interlocking fit. The extensions 203 and 211 can be made enlarged for a friction or snap fit with respect to the rectangular depressions 205 or 213.

Figures 27, 28, 29:
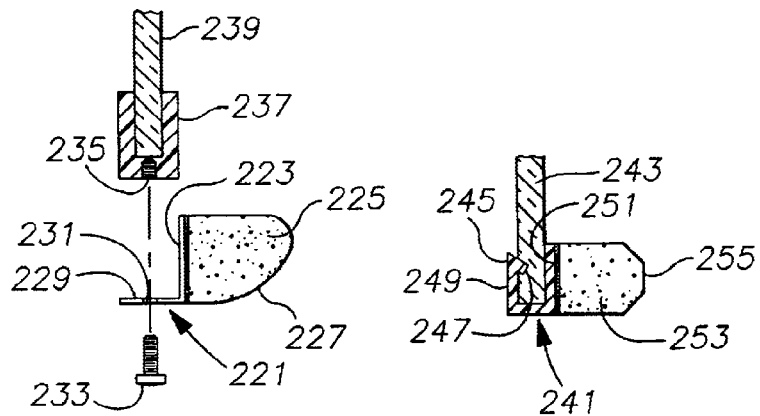
FIG. 27 illustrates a side sectional view of a bottom fitting protrusion member having a general "L" shape and including a vertical member from which a rearwardly extending and shaped sealing member extends having a more gently sloping lower side, and a horizontal member having an aperture for engagement with a threaded member extending through to a threaded bore into the bottom surface of a lens or lens support to secure the protrusion member to the lens or lens support.
FIG. 28 is a side sectional view similar to that seen in FIG. 25 and in which at least a portion of a channel in the lower forward portion of a lens or lens support is engaged by a laterally hook shaped structure extending from the top and one side of a clip-shaped or "U" shaped channel member having a sloping upper portion leading to an extension rib for facilitating the engagement of the channel shaped protrusion member from the lower portion of a lens or lens support.
FIG. 29 is a side sectional view of a rearwardly fitting protrusion member having one of hook and loop members attached to a forward surface thereof and a rearward surface of a lens or lens support having the other one of hook and loop members to engage the protrusion member to the lens or lens support.

Referring to FIG. 27, a side sectional view of a bottom fitting protrusion member 221 having a general "L" shape and including a vertical member 223 from which a rearwardly extending and shaped sealing member 225 extends having a more gently sloping lower side 227, and a horizontal member 229 having an aperture 231 for engagement with a threaded member 233 extending through to a threaded bore 235 into the bottom surface of a lens support 237 surrounding a lens 239. The threaded members 233 are expected to be small, about the same size as the threaded members used for eyewear hinges. The lower curved surface 227 of the sealing member 225 provides a surface which matches more nearly with the face of the user as the sealing member 225 undergoes some upward deformation to build the slight force which aids sealing.

Referring to FIG. 28 a side sectional view similar to that seen in FIG. 25 and in which at least a portion of a somewhat "U" shaped and hook shaped and channeled protrusion member 241 is attached at the lower portion of a lens 243. The lens 243 also carries a small groove 245 which is engaged by a hook shaped cross sectional upper portion 247 of a front wall 249. The upper continuous slope of the upper portion 247 aids in snapping the protrusion member 241 in place. A rear wall 251 of the protrusion member 241 is attached with a rearwardly extending sealing member 253 having a hemi-octagonal rear surface 255 including a top surface, upper 45° angled surface, rear surface lower 45° angled surface and lower surface, the upper and lower surfaces extending back to the rear wall 251.

Referring to FIGS. 29, a side sectional view of a rearwardly fitting protrusion member 261 having or even merely consisting of one of hook and loop members 263 attached to a forward surface of a protrusion member or directly to a sealing member 265 and a rearward surface of a lens 267 the other one of hook and loop members 269 to engage the one of hook and loop members 263.

Figures 30, 31, 32:
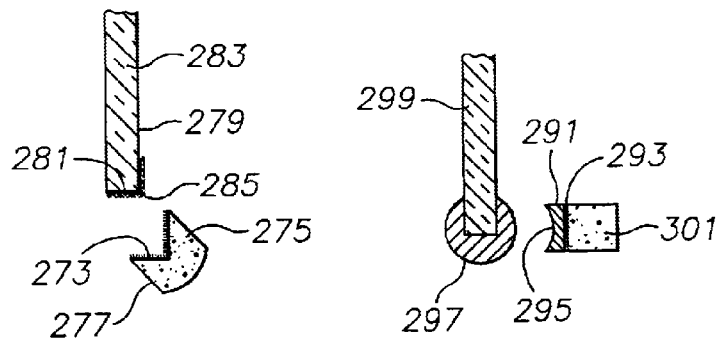
FIG. 30 is a side sectional view of a rearwardly and downwardly fitting "L" shaped protrusion member having one of hook and loop members attached to a forward and upward surface thereof and shown with respect to a rearward and downward surface of a lens or lens support having the other one of hook and loop members to engage both the forward and upward surface of the protrusion member to the lens or lens support, and a rearwardly and downwardly extending sealing member having a terminal curved surface.
FIG. 31 is a side sectional view of a rearwardly fitting magnetic protrusion member having a rearward flat side and a curved front opposite side for attachment to a magnetic or metallic curved portion of a lens support having a curved surface complementary to the curved front of the magnetic protrusion member and including a rearwardly extending rectangular cross shaped sealing member.
FIG. 32 is a side sectional view of a rearwardly fitting magnetic lens support member having a rearward side and forward side attached to a lens by glue, bonding or any other method, and a magnetic protrusion member having a magnetic characteristic of complementary polarity to the magnetic lens support member.

FIG. 30 is a side sectional view of a rearwardly and downwardly fitting "L" shaped protrusion member 271 having one of hook and loop members 273 attached to a forward 275 and upward 277 surface thereof and shown with respect to a rearward surface 279 and a downward surface 281 of a lens 283 having the other one of hook and loop members 285 to engage both the forward and upward surface of the one of hook and loop members 273.

FIG. 31 is a side sectional view of a rearwardly fitting magnetic protrusion member 291 having a rearward flat side 293 and a curved front opposite side 295 for attachment to a curved lower portion of a metallic lens support 297 supporting lens 299 having a curved surface complementary to the curved front of the protrusion member 291 and including a rearwardly extending rectangular sealing member 301.

Referring to FIG. 32, a side sectional view of a rearwardly fitting magnetic lens support member 303 having a rearward side 305 and forward side 307. The magnetic lens support member 303 is shown attached to a lens 309 by glue, bonding or any other method. A magnetic protrusion member has a magnetic characteristic of complementary polarity to the magnetic lens support member 303, and is attached to a rearwardly extending downwardly curving sealing member 313. A downwardly and rearwardly sloping surface 315 transitions into a downwardly curved surface 317 to provide a supported sealing with a face of the user.

Figures 33, 34, 35:
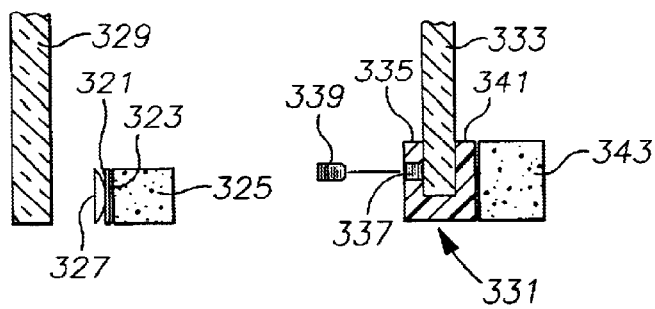
FIG. 33 is a side sectional view of a rearwardly fitting suction cupped protrusion member having a rearward surface and a forward suction cup for attachment to a curved lower portion of a lens or lens support and including a rearwardly extending rectangular sealing member.
FIG. 34 is a side sectional view of a "U" shaped channel protrusion member engaging the bottom of a lens or lens support with a forward side of the channel having a forward threaded bore engaged by a set screw and a rearward side of the channel having a rearwardly extending rectangular sealing member.
FIG. 35 is a side sectional view of a "U" shaped channel protrusion member engaging the bottom of a lens or lens support with a rearward side of the channel having a rearward threaded bore engaged by a set screw and a rearward side of the channel having a rearwardly extending rectangular sealing member having an access bore in alignment with the threaded bore for admission and insertion of the set screw.

Referring to FIG. 33 is a side sectional view of a rearwardly fitting suction cupped protrusion member 321 having a rearward flat surface 323 for attachment to a rectangular cross sectional shaped sealing member 325. A frontal suction cup 327 is seen opposing a lens 329.

FIG. 34 is a side sectional view of a "U" shaped channel protrusion member 331 engaging the bottom of a lens 333 with a forward side 335 of the channel protrusion member 331 having a forward threaded bore 337 engaged by a set screw 339 and a rearward side 341 of the channel protrusion member 331 having a rearwardly extending rectangular sealing member 343. The channel protrusion member 331 is held in place by the compressive and biting force of the set screw 339 against the lens 333.

FIG. 35 is a side sectional view of a "U" shaped channel protrusion member 351 engaging the bottom of a lens 353 with a rearward side 355 of the channel protrusion member 351 having a rearward threaded bore 357 engaged by a set screw 359. The rearward side of the channel protrusion member 351 also having a rearwardly extending rectangular sealing member 361 having an access bore 363 in alignment with the threaded bore 357 for admission and insertion of the set screw 359.

Figure 36:
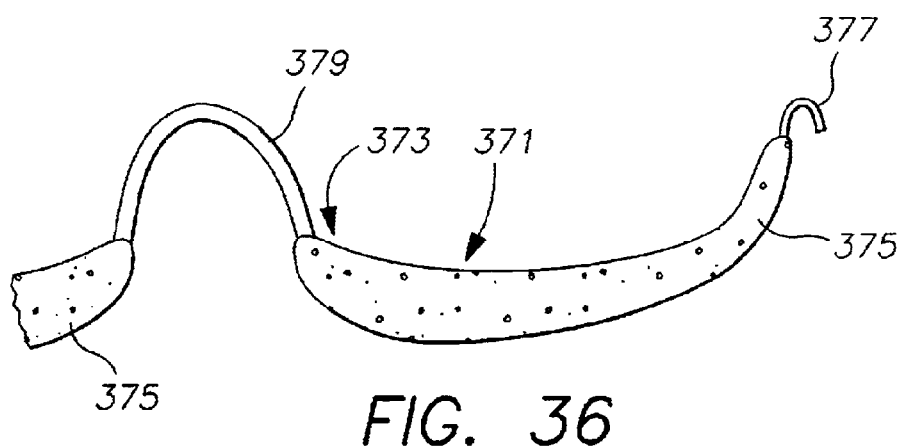
FIG. 36 is a rear view of the right two thirds of an extended protrusion member and sealing member having a structural protrusion portion including a suspension nose bridge and side hooks for engaging the forward temple members of eyewear, and an attached rearwardly extending sealing member of rounded shape supported by the portions of the protrusion member between the suspension nose bridge and side hooks.

FIG. 36 is a rear view of the right two thirds of an extended assembly 371 including a protrusion member 373 and sealing member 375. The left half of the member 371 is a mirror image of the shown right half. The protrusion member 373 extends from a hook end 377 and a suspension nose bridge 379 and then to an opposite hood end 377 (not shown). The assembly 371 is intended to be suspended between the two arms of the temple portions of eyewear, and also supported at the middle by the suspension nose bridge 379 either against the user's nose or against some other structure.

Figure 37:
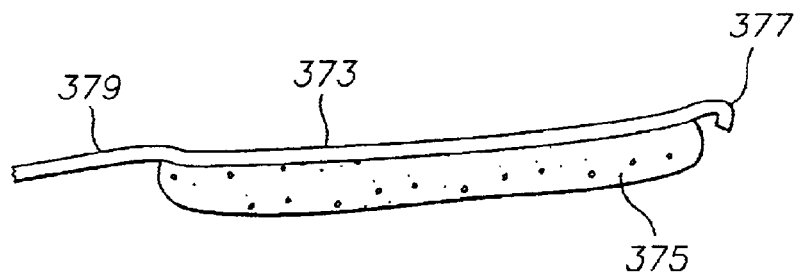
FIG. 37 is a downward view of the extended protrusion member of FIG. 36.
Figure 38:
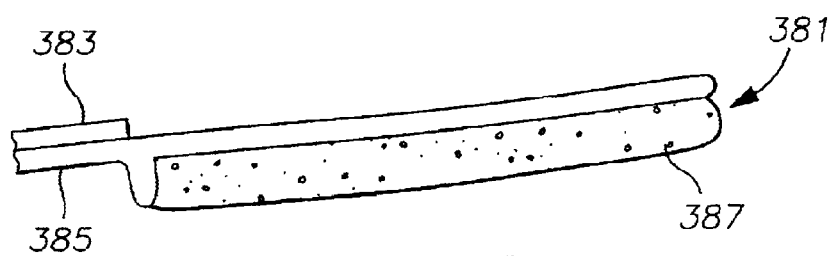
FIG. 38 is a top view of the right two thirds of an extended molded integral protrusion and sealing member having an integrally molded forward lens engaging portion 27 and a rearwardly extending nose bridge engagement portion integral with the protrusion member.

The attached rearwardly extending sealing member 375 can be of rounded shape and supported to any extent by the portions of the protrusion member 373, including having the sealing member 375 surround the protrusion member 373 and partially surround the protrusion member 373. Referring to FIG. 38, a downward view of the assembly 371 and extended protrusion member 373 of FIG. 37 is shown.

Figure 39:
FIG. 39 is a top view of the right two thirds of an extended molded integral protrusion and sealing member having an integrally molded forward "U" shaped lens engaging portion and a rearwardly extending nose bridge engagement portion.

FIG. 39 is a top view of the right two thirds of an extended molded integral protrusion and sealing member 381 having an integrally molded forward lens engaging portion 383 and a rearwardly extending nose bridge engagement portion 385 integral with the molded integral protrusion and sealing member 381. The left half of the member 381 is a mirror image of the shown right half. The differing portions of the molded integral protrusion and sealing member 381 need not be of the same hardness, and reinforcement dipping and treatment is permissible to give a sealing portion 387 hardness different than the protrusion support portions.

FIG. 39 is a top view of the right two thirds of an extended molded integral protrusion and sealing member 391 having an integrally molded forward "U" shaped lens engaging portion 393 and a rearwardly extending nose bridge engagement portion 395. The left half of the member 391 is a mirror image of the shown right half. A sealing portion 397 can be softer or harder than integrally molded forward "U" shaped lens engaging portion 393, and reinforcement dipping and treatment is permissible.

Figure 40:
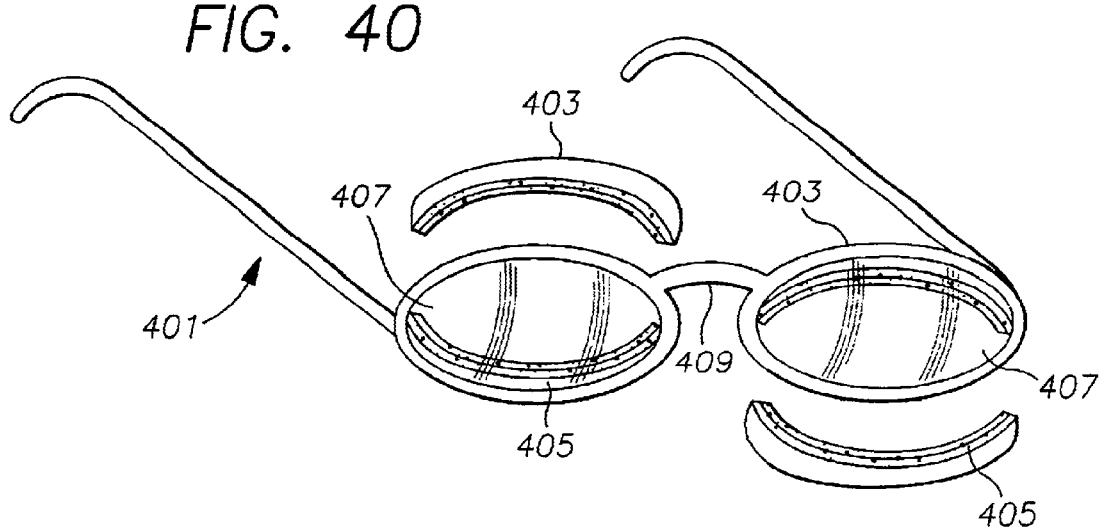
FIG. 40 is a perspective view of a set of conventional spectacles having single lens upper and lower engagement members immediately above and below individual separated lens areas.

FIG. 40 is a perspective view of a set of conventional spectacles 401 having single lens structure upper and lower sealing members 403 and 405 immediately above and below an individual separated lens 407 structure. The sealing members 403 and 405 do not cross the center of a bridge structure 409.

Figure 41:
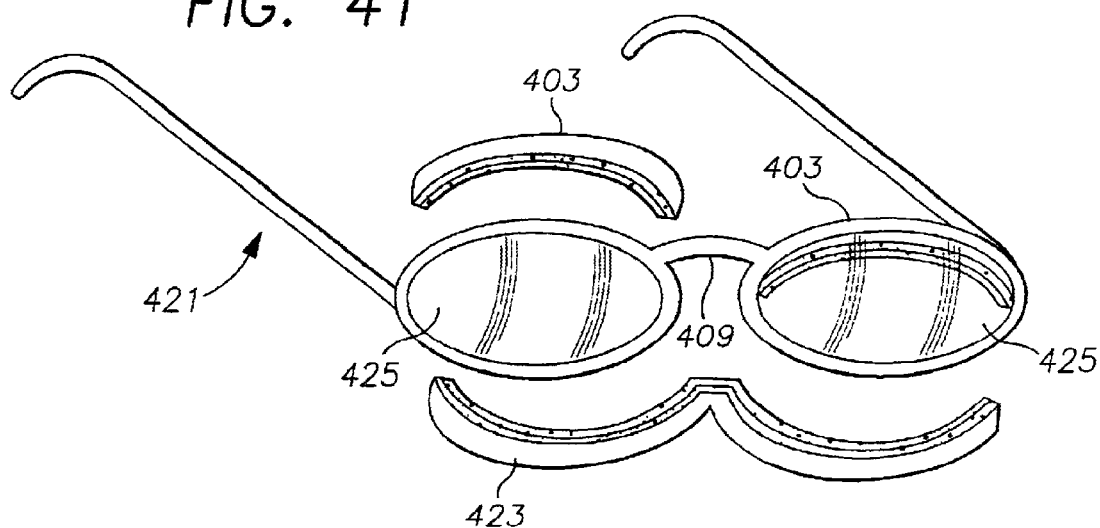
FIG. 41 illustrates a set of conventional spectacles utilizing a lower engagement member extending across both individual separated lens areas utilized in conjunction with a single lens upper engagement member.

FIG. 41 illustrates a set of conventional spectacles 421 utilizing a lower sealing member 423 extending across both individual separated lens areas 425 utilized in conjunction with individual single lens upper sealing members 403 as were seen in FIG. 40.

Figure 42:
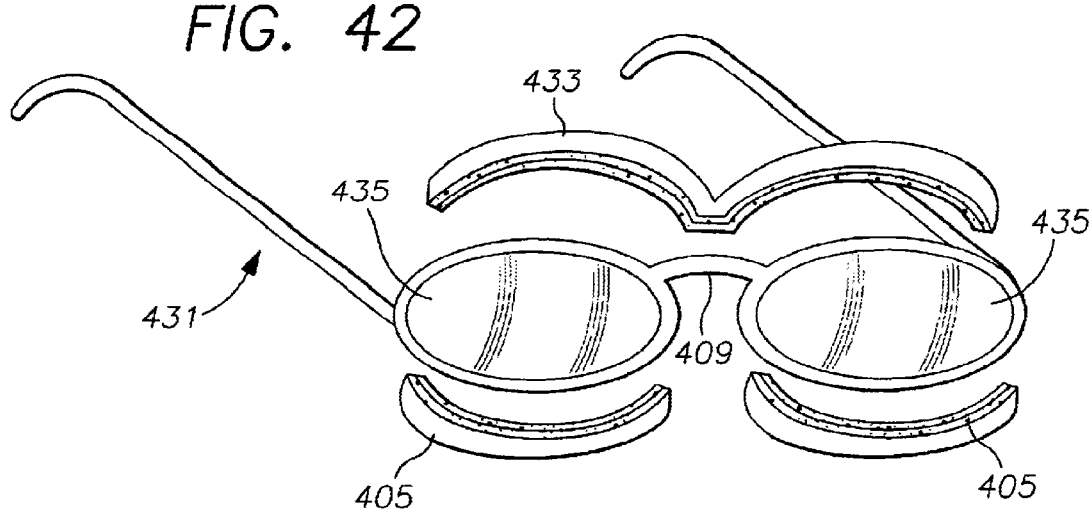
FIG. 42 illustrates a set of conventional spectacles utilizing an upper engagement member extending across both individual separated lens areas utilized in conjunction with a pair of single lens lower engagement members.

FIG. 42 illustrates a set of conventional spectacles 431 utilizing an upper sealing member 433 extending across both individual separated lens areas 435. The upper sealing member 433 is utilized in conjunction with a pair of single lens lower sealing members 405 as were seen in FIG. 40.

Figure 43:
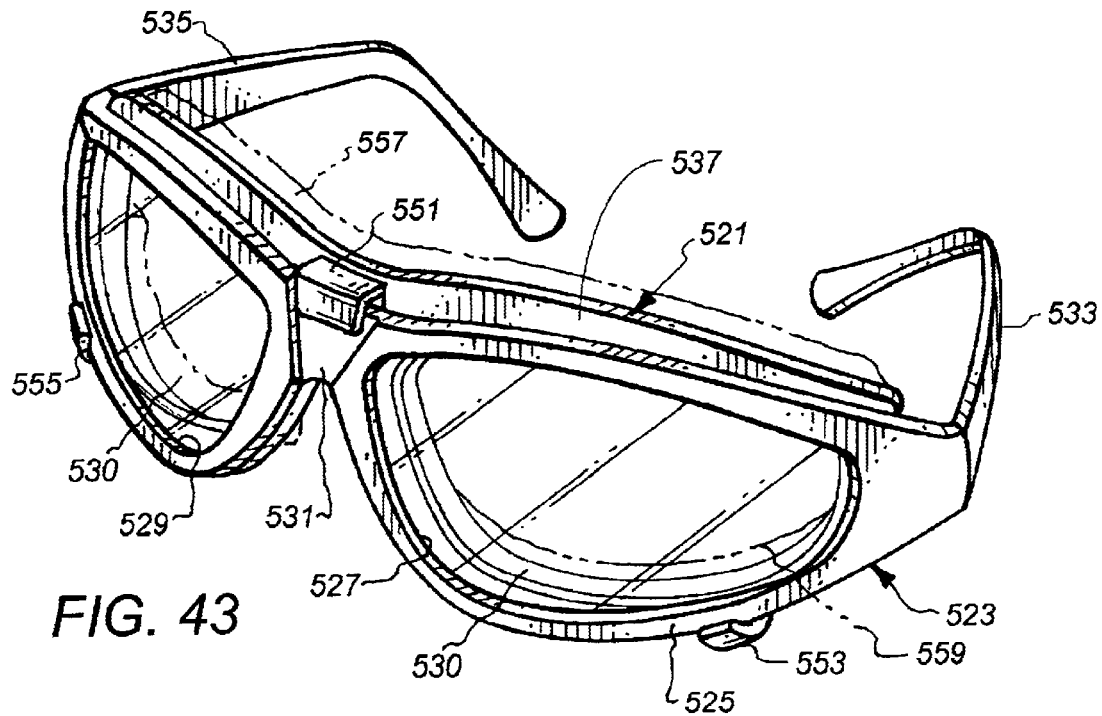
FIG. 43 is an perspective view of a typical pair of eyeglasses on which has been mounted an embodiment of eyewear member.
Figure 44:
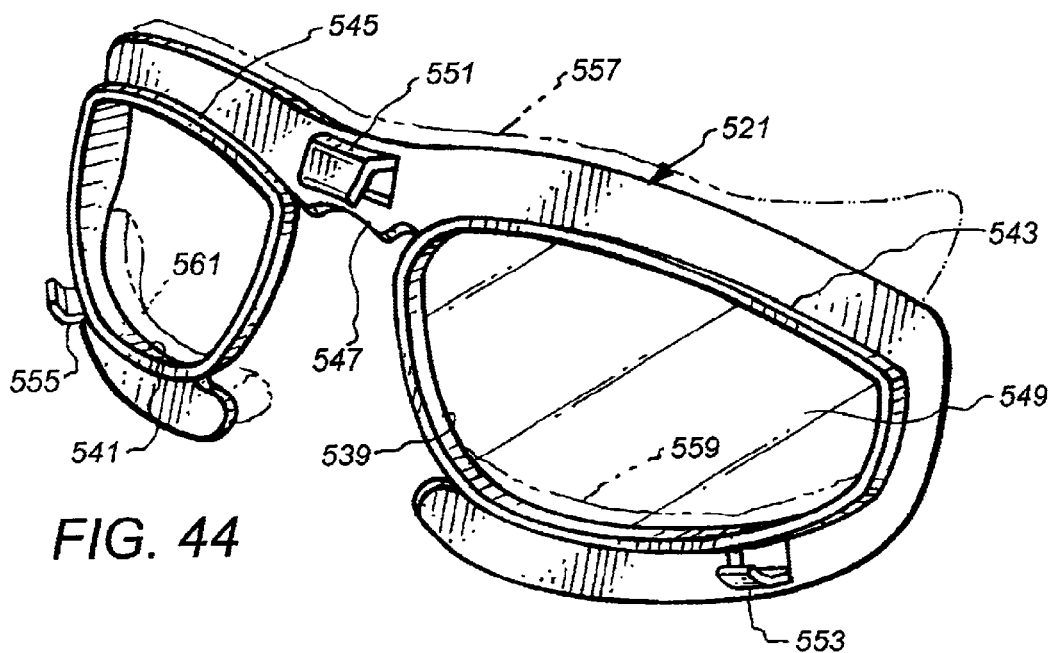
FIG. 44 is a frontal perspective view of an embodiment of eyewear member of the present invention showing the partial peel up of a removable seal.

Referring particularly to the drawings, there is shown in FIGS. 43 and 44 an embodiment of an eyewear member 521 of this invention. Each of the eyewear members defined within this invention are to be connectable to a conventional pair of eyeglasses 523. The conventional pair of eyeglasses 523 is formed of a front section, which is called a rim 525. The rim 525 includes a pair of similarly shaped and similarly sized lens openings 527 and 529. Within each lens opening 527 and 529 is a lens 530. Separating the lens openings 527 and 529 is a rim 24 which includes a bridge 531. A left temple earpiece-533 is pivotally connected to the left side of the rim 525. A right temple earpiece 535 is pivotally connected to the right side of the rim 529.

An embodiment is formed of an eyewear member 521. The eyewear member 537 includes a pair of similarly sized and shaped enlarged openings 539 and 541. Each of the openings 539 and 541 is basically of the same size and the same configuration as lens openings 527 and 529 with enlarged openings 539 to be alignable with the lens opening 527 and enlarged opening 541 to be alignable with the lens opening 529. The lens opening 539 is defined by a peripheral flange 543. The lens opening 541 is defined by a peripheral flange 545. The peripheral flange 543 may be integrally connected to the eyewear member 521. The peripheral flange 545 may be integrally connected to the eyewear member 521. The eyewear member 521 includes a bridge 547 which is located between peripheral flanges 543 and 545. The peripheral flanges 543 and 545 are designed to function as a lock between the eyeglasses 523 and the embodiment of the eyewear member 521 but are not required in all embodiments. Also, peripheral flanges 543 and 545 can operate as lifters, either integrally connected to the eyewear member or being removable from the eyewear member. The peripheral flanges 543 and 545 are designed to connect with the edge of the rims 525 which mounts each of the lenses 530. In other words, the peripheral flanges 543 and 545 are designed to abut against the lens openings 527 and 529.

If the eyeglasses 523 included prescription lenses 530 there would probably be no need to include any lens within either of the enlarged openings 539 and 541 with the enlarged openings 539 and 541 being open unless the lenses of 28 were of a clear nature, and therefore the possibility of tinted, non corrective vision lenses may be included in either of the enlarged openings 539 and 541. In the situation where the lenses 530 are piano, a user may want to include a prescription lens 549 within enlarged opening 539 and also a separate prescription lens, which is not shown, within enlarged opening 541.

Extending outward from the front surface of the eyewear member 521 is a shaped hook member 551, Hook member 551 is mounted on the support structure 521 at the bridge 547. On the left side of the eyewear member 521 and located at the bottom edge of the eyewear member 521 is a similarly shaped angled projection member 553 is seen. On the right side of the eyewear member 521, also at the bottom edge of the eyewear member 521, is a shaped angled projection member 555 is seen. The perspective view of the three angled projection members 551, 553 & 555 enables a good view of both the front, back and side of their shape. The angled projection members 551, 553 & 555 are to engage with the eyeglasses 523 with the eyewear member 521 being mounted adjacent the inside surface of the rim 525. When attached, the shaped angled projection member 551 connects with the bridge 531 of the eyewear 523. The shaped angled projection member 553 connects with the rim 525 directly adjacent the lens opening 527. The angled projection member 555 engages with the rim 525 directly adjacent the lens opening 529. As a result, the angled projection members 551, 553 & 555 function to fixedly mount the eyewear member 521 to the eyeglasses 523. However, the user is fully capable of disengaging the eyewear member 521 from the eyeglasses 523 when usage of the eyewear member 521 is not required. Normally, the rearward surface of the eyewear member 521, facing the face of the wearer, may include an elongated cushioning strip 557 located directly adjacent the top edge of the eyewear member 521. The eyewear member 521 along the bottom edge thereof directly adjacent the enlarged opening 539 will also normally include a cushioning strip 559. The eyewear member 521 directly adjacent the enlarged opening 541 also includes a cushioning strip 561. The function of the cushioning strips 557, 559 and 561 is to provide a close fit against the user's face. The cushioning strips 559 and 561 may connect with the cushioning strip 557 if it is desired to provide a complete seal with the user's face. Also, there may be cushioning strips that extend along side the nose opening underneath to the bridge 547. The cushioning strips 557, 559 and 561 may be located instead or also between the eyewear member 521 and the eyeglasses 523 if such location is desired.

Figure 45:
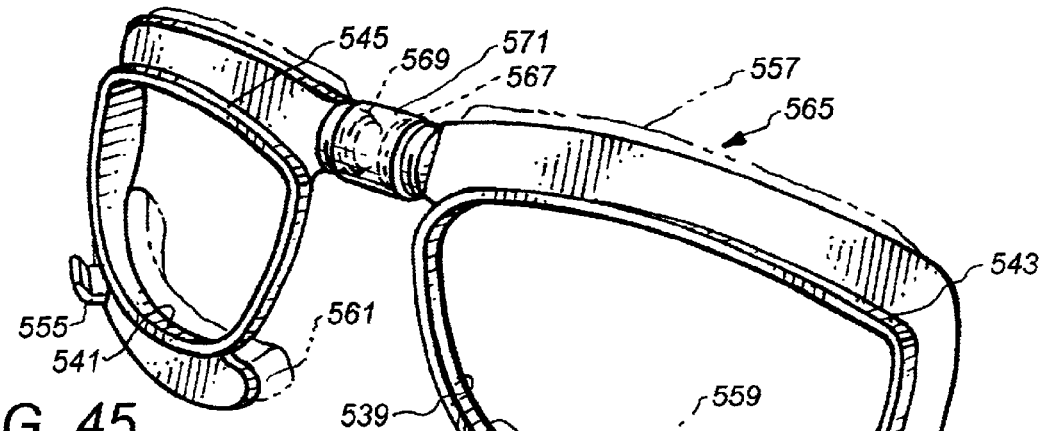
FIG. 45 is an perspective view of a second embodiment of eyewear member of the present invention.

Referring particularly to FIG. 45 of the drawings, there is shown the second embodiment as an eyewear member 565. Like numerals have been utilized for like parts. However, the eyewear member 565 does not include the shaped angled projection member 551 but does include the shaped angled projection members 553 and 555. The eyewear member 565 is separated into two substantially equal parts with enlarged opening 539 being located separate from the enlarged opening 541. There may be certain situations in which the user may desire to use only one of the enlarged openings 539 or 541, and in that situation, the eyewear member 565 could be utilized. The eyewear member 5651 is broken in the area of the bridge 547 and has a pair of rounded members 567 and 569. The rounded members 567 and 569 can be interconnected together by a sleeve 571 which telescopingly connects between the rounded members 567 and 569. By using the sleeve 571, the user can achieve a structure which is basically similar to an embodiment eyewear member 521.

Figure 46:
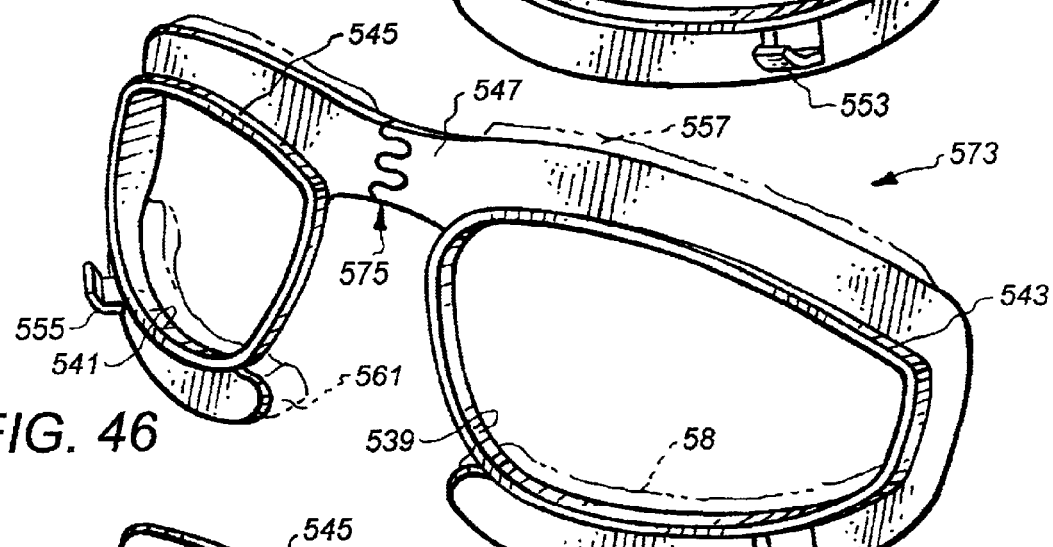
FIG. 46 is a frontal perspective view of a third embodiment of eyewear member of the present invention.

Referring particularly to FIG. 46 of the drawings, there is shown a further embodiment as eyewear member 573. The third embodiment 573 again uses like numerals from the eyewear member 521 to refer to like parts. Eyewear member 573 is also separable into two parts similar to the eyewear member 565. However, the structure to achieve the separation comprises an interlocking tongue and groove arrangement 575 located at the bridge area 547. The tongue and groove arrangement 575 can be merely pulled apart, possibly with some lateral disjoining motion, and then reconnected with the user assuming a solid interconnection when reconnected.

Figure 47:
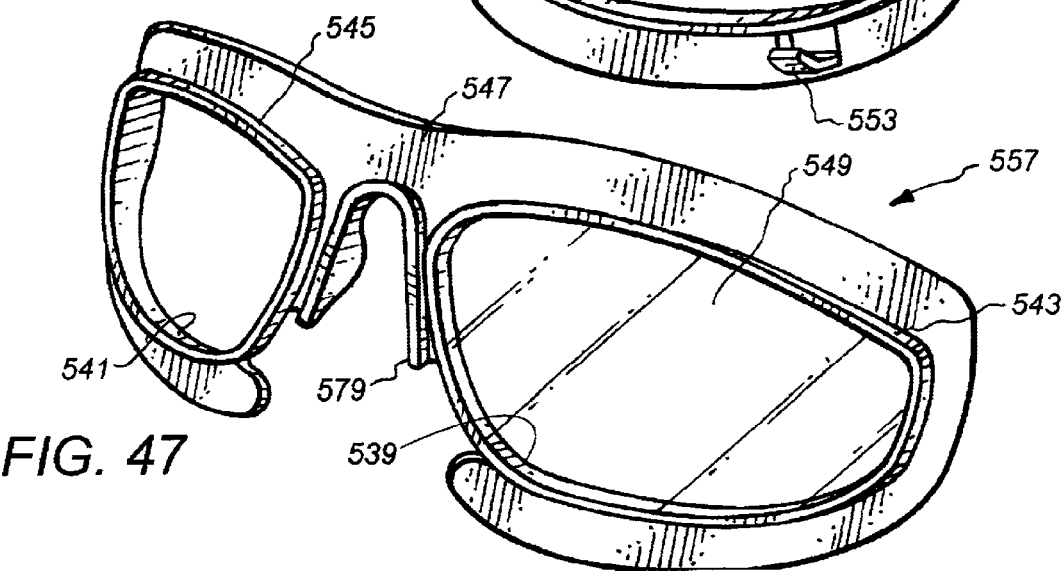
FIG. 47 is an perspective view of a fourth embodiment of eyewear member of the present invention.

Referring particularly to FIG. 47 of the drawings, there is shown a fourth embodiment as an eyewear member 577. The fourth embodiment again utilizes reference numerals for the same parts as was used in conjunction with an embodiment 521. The distinction of this embodiment is that there are no angled projection members, such as angled projection members 553 and 555 to facilitate mounting to the eyeglasses 523. However, included within the nose opening area below the bridge 547 is a shaped nosepiece 579. The nosepiece 579, by being mounted on the nose of the user, can function to mount the eyewear member 577 to the eyeglasses 523. However, with the eyewear member 577, there is no direct attachment between the to the eyeglasses 523. The only attachment is through the nosepiece 579 which fixes the position of the eyewear member 577 on the face of the user with respect to the eyeglasses 523. The nosepiece 579 could be used to connect directly to the bridge 531 of the eyeglasses 523. In other words, the nosepiece 579 could be used as a registering mount for the eyeglass 523 if such is desired.

Figure 48:
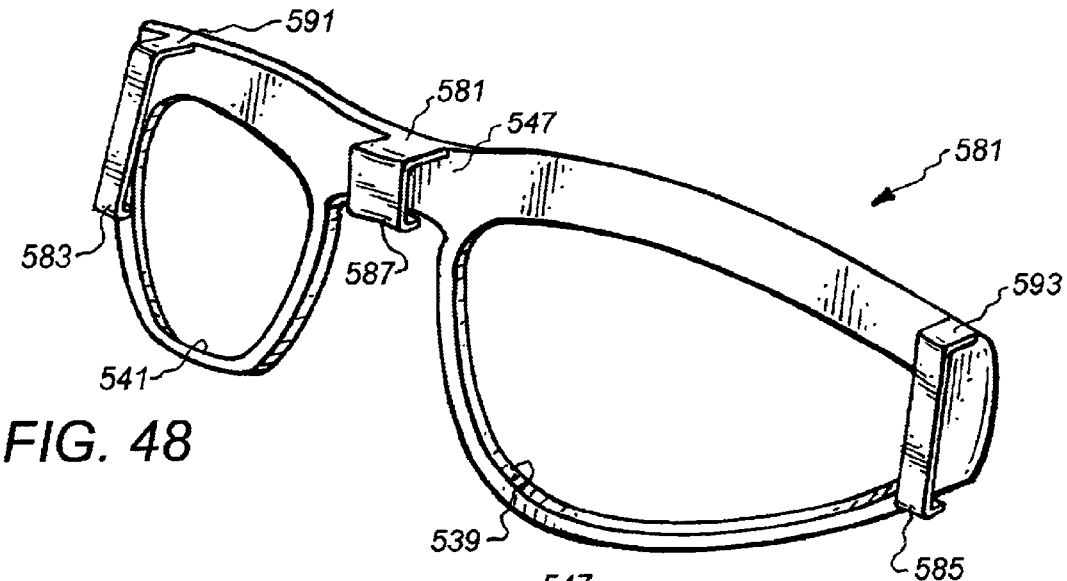
FIG. 48 is an frontal perspective view of a fifth embodiment of eyewear member of the present invention.

Referring particularly to FIG. 48 of the drawings, there is shown a fifth embodiment as an eyewear member 581. Again, like numerals have been used to refer to like parts when compared to an embodiment 521. The structure of the attachment utilized in conjunction with eyewear member 581 may constitute a series of deflectable clips, such as end clips 583 and 585 and a nose clip 587. The nose clip 587 can be physically bent about a "living hinge axis" 589 to permit entry of the bridge 531 of the eyeglasses 523 so that the bridge 531 will then be captured when the nose clip 587 is released. The end clip 583 can be bent in a similar manner by a "living hinge axis" 591 and the end clip 593 can be bent in a similar manner by a "living hinge axis" 593. The end clip 583 is to be located about the right side edge of the eyeglasses 523. The end clip 585 is to be located about the left side edge of the eyeglasses 523.

Figure 49:
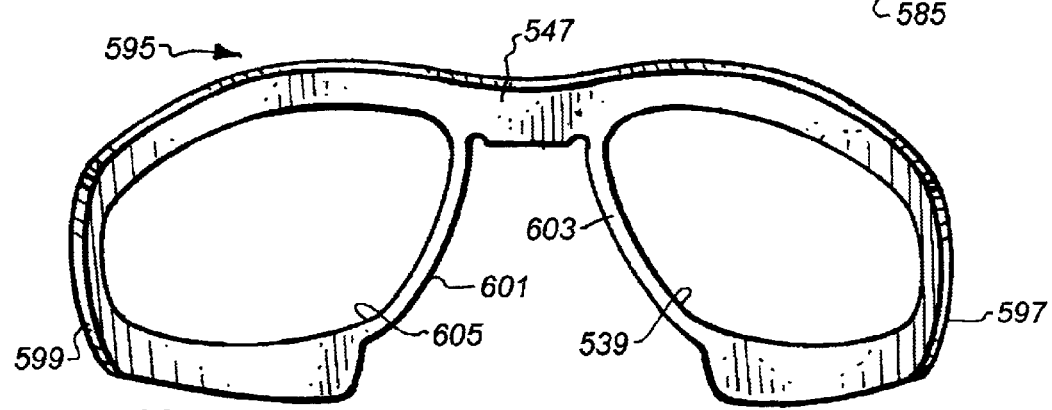
FIG. 49 is a rear view of a sixth embodiment of eyewear member of the present invention which would be the view of the attachment from the face of the user when attachment.

Referring particularly to FIG. 49 of the drawings, there is shown a sixth embodiment, seen as an eyewear member 595. Again, like numerals are utilized to refer to like parts. The eyewear member 595 constitutes a thin walled eyewear member structure with the right side of the eyewear member 595 being bent upwards forming bent end 597 and the left side of the eyewear member being similarly bent inward forming bent end 599. The forming of bent ends 597 and 599 are also similarly formed with respect to the manner in which the basic support structure of the eyewear members 521, 565, 573, 577 and 581. The eyewear member 595 could be impregnated with a magnetic material which could be used to hold the eyewear member 595 to the eyeglasses 523 where the eyeglasses 523 were made of ferromagnetic material. However, eyewear member 595 could also include small bar magnets imbedded within the structure of the eyewear member 595 eyewear member 521. The eyewear member 595 could also be constructed of a readily bendable material and not necessarily a completely rigid material. The permitting of bending or deflection of the eyewear member 595 is to facilitate stowage in one's pocket or purse and also to facilitate a close attachment to different designs of eyeglasses 523. The eyewear member 595 could also be mounted by interlocking with a nosepiece, which is not shown, which would be mounted in conjunction with the eyeglasses 523.

Note also the presence of nosepiece sidewalls 601 and 603, each of which supports a vertically expanded portion 605 seen below.

Figure 50:
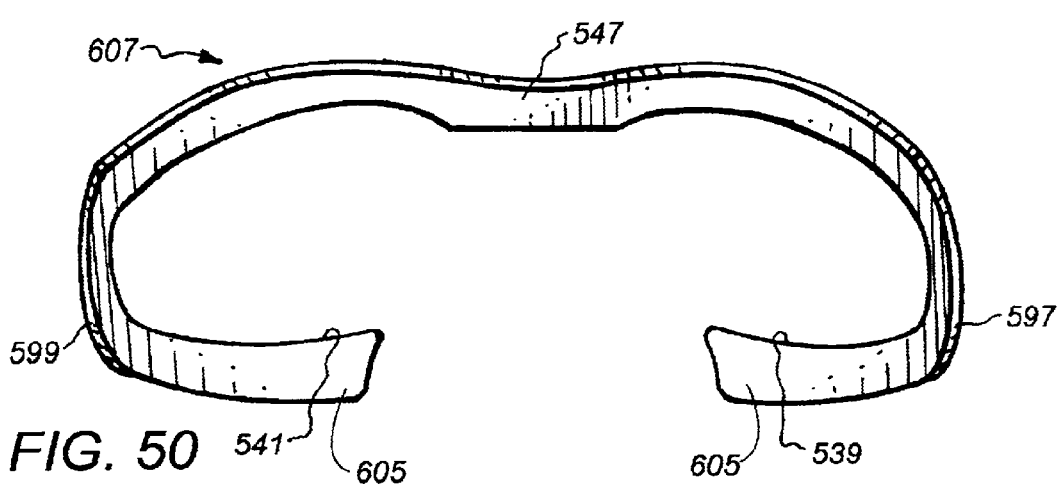
FIG. 50 is a rear view of a seventh embodiment of eyewear member of the present invention.

Referring particularly to FIG. 50 of the drawings, there is shown a seventh embodiment as a eyewear member 607. The eyewear member 607 is basically similar to the eyewear member 595 with the exception that the nosepiece sidewalls 601 and 603 have been removed, but where the vertically expanded portions 605 remain. Some users may prefer the more open configuration of the eyewear member 607 as opposed to an embodiment where the enlarged openings 539 and 541 are completely enclosed, as is shown for eyewear member 595.

Figure 51:
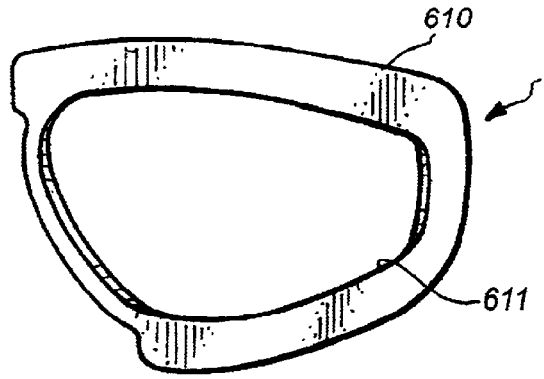
FIG. 51 is a front view of an eighth embodiment of eyewear member of the present invention.

Referring particularly to FIG. 51 of the drawings, there is shown an eighth embodiment, seen as a eyewear member 609. Eyewear member 609 has a body 610 having a single enlarged opening 611. In most instances, the user will have a pair of the eyewear members 609, one for each associated side of an eyeglasses 523. The primary advantages of eyewear member 609 is that two in number of the eyewear member 609 is smaller in size than a single double sized embodiment, as has been shown in FIGS. 43–50. Also, by using of a single half-size embodiment as the eyewear member 609 which is capable of connecting to a wider range of eyeglasses 523 that have various shapes and sizes, especially the separation of the lenses 549.

Figure 52:
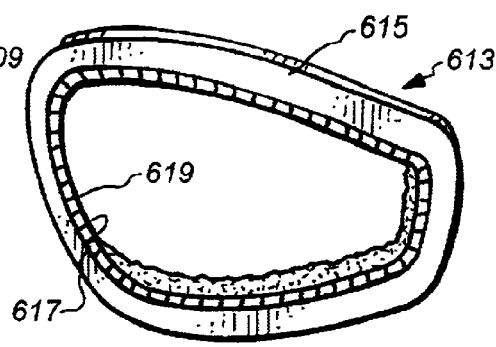
FIG. 52 is a front view of a ninth embodiment of eyewear member of the present invention.

Referring particularly to FIG. 52 of the drawings, there is shown a ninth embodiment as an eyewear member 613. The eyewear member 613 is a representation of a half size eyewear member 613 similar to eyewear member 609 of FIG. 51. One advantage of the eyewear member 613 is that the body structure wall surface 615 has an enlarged opening 617 and including a vented cushioning material 619. The venting of the cushioning material 619 is aided by including a series of slats within the material 619. The purpose of the venting is to provide access by air to the area of the user's eye, as well as an exit for moisture, primarily to prevent fogging.

Figure 53:
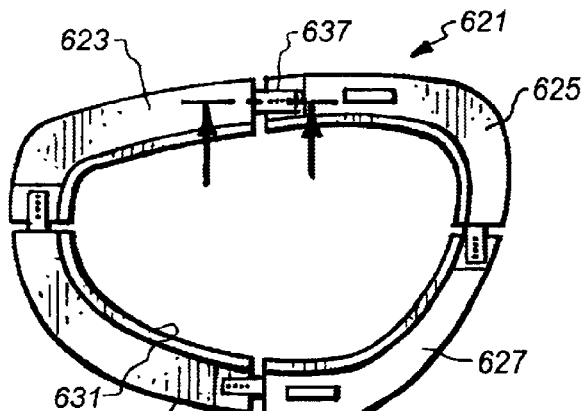
FIG. 53 is a front view of a tenth embodiment of eyewear member of the present invention which provides for adjustment of the eyewear member to increase or decrease the size of the eyewear member and thereby enlarge or decrease the size of the opening enclosed by the eyewear member.
Figure 54:
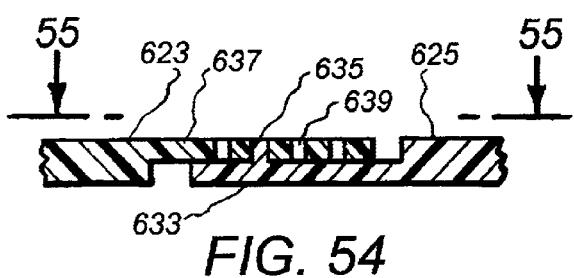
FIG. 54 is a cross-sectional view taken along line 54—54 of FIG. 53.
Figure 55:
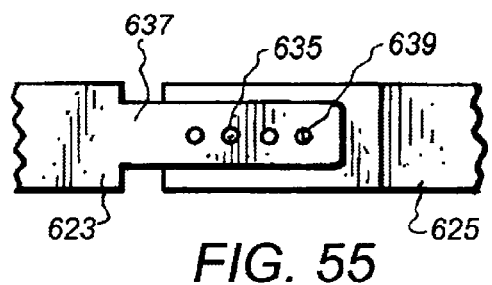
FIG. 55 is a view of the adjustment mechanism used in the tenth embodiment of FIG. 53 taken along line 55—55 of FIG. 54.

Referring particularly FIGS. 53–55 of the drawings, there is shown a further embodiment as eyewear member 621 of this invention. Eyewear member 621 is shown as having an overall size and structure as a half size eyewear member similar to the eyewear member 609 shown in FIG. 51. It is considered to be within the scope of this invention that the structural arrangement of the eyewear member 621 can be incorporated within the double shaped eyewear members 521, 565, 573, 577, 581, 595, and 605, shown in FIGS. 43–50. Instead of having a single structure as was seen in FIGS. 51 and 52, the eyewear member 621 has a structure which is shown as being divided into four separate segments. The division can be accomplished with fewer or more than four separate segments, particularly depending upon the manner in which the segments are joined. The segments are labeled as eyewear member segments 623, 625, 627 and 629. Segment 623 is connected to segment 625 in precisely the same manner as the other segments. The segments 623, 625, 627 and 629 cooperate together to enclose enlarged opening 631. The interconnection between the segments is more accurately depicted in FIGS. 54 and 553. Segment 625 is shown having a flange 633 which is about one-half the thickness of the segment 625. The flange 633 includes an-upstanding pin 635. The segment 623 has also a one-half thickness flange 637. Flange 637 has a series of holes 639. A hole 639 is selected to connect with the pin 635. By locating the pin 635 in the various holes 639, the size of the enlarged opening 631 can be expanded and contracted. This provides for adjustment of the enlarged opening 631 to accommodate eyeglasses 523 which have smaller lenses 530 or larger lenses 530.

Figure 56:
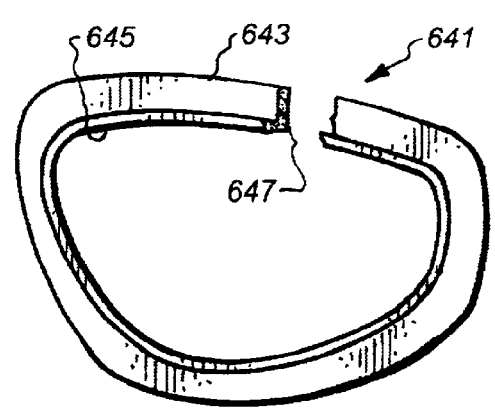
FIG. 56 is a front view of an eleventh embodiment of eyewear member of the present invention which uses a magnet to function as a securement to eyeglasses.

Referring particularly to FIG. 56 of the drawings, there is a further embodiment seen as eyewear member 641. Eyewear member 641 includes a body 643 enclosing an enlarged opening 645. The material of construction of the eyewear member 641 may also include magnetized material 647. The eyewear member 641 may be secured to eyeglasses 523 that are formed of ferrous material so that the eyewear member 641 will be drawn to and held in position solely by magnetic force on the eyeglasses 523.

Figure 57:
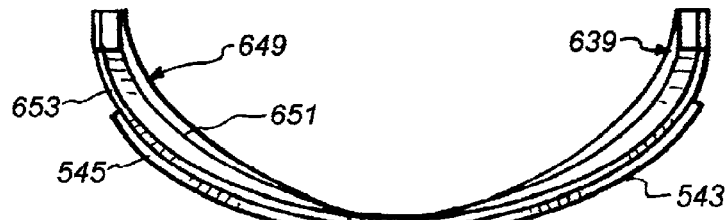
FIG. 57 is a top plan view of a eyewear member of the present invention on which has been mounted lifters for obtaining a close fit with the face of a user.

Referring particularly to FIG. 57 of the drawings, there is shown the additional structure of lifters 649. Each lifter 649 comprises a length of sealing material 651 fixedly mounted on a base 653. Base 653 may be attached to the support structure of eyeglasses 523. The function of the lifters 649 is to take up any gap area that is created between the user's face and the support structure of the eyeglasses 523 so an to achieve an essentially airtight seal with the user's face. The lifters 649 are to be applied to eyeglasses 523 any conventional means, each as adhesive, magnetic attraction, pins and bores, hook and loop, mechanical attachments and the like.

Referring particularly to FIGS. 58 and 59 of the drawings, there is depicted the left eye section of an embodiment eyewear member 521 which has been modified to a current embodiment seen as eyewear member 655. Eyewear member 655 is modified for mounting on a wearer's ears by temple members 657 as in FIG. 58, or around a wearer's head with a strap 659 as seen in FIG. 59. Eyewear member 655 may also include corrective vision lenses 549. The embodiment of FIGS. 58 and 59 may be used when a user is using the a conventional pair of sunglasses or eyewear 523 which contain plano lenses. When the user moves from a sunny environment to a more darkened environment, such as when the user would go indoors and the user desires to take off his or her sunglasses, the user can then utilize the eyewear member 655 and support such on the user's face. This can be accomplished by temple earpieces 657 or strap 659. The temple earpieces 657 are to be removably secured to the eyewear member 655. The user is to be able to pull the earpieces out from pocket or purse and connect such to the eyewear member 655. In essence, now the essential construction seen in an embodiment as eyewear member 521 is being used not as an attachment to eyeglasses 523 but as a pair of eyeglasses in their own right. Instead of the temple members 657, the user could connect a strap 659 to the eyewear member 655 with the strap 659 being designed to encompass the user's head and support an embodiment eyewear member 655 on the user's head. It is to be understood that the structure of FIGS. 58 and 59 could be incorporated with any embodiment of this invention, including any features of any embodiment disclosed herein. The strap 659 may will normally comprise fabric, stretch fabric, elastic cloth or similar type of material.

Referring particularly to FIGS. 60–62 of the drawings, there is shown a further embodiment seen as a eyewear member 671. Eyewear member 671 again uses the same reference numbers that were used in reference in an embodiment 521 to refer to similar parts. FIG. 60 shows only the left eye section of the eyewear member 671. An adjustable angled projection member set 673 is seen as having a pair of vertical flanges 675 supporting an adjustable angled projection member 677. Each of the angled projection members 551, 553, and 555 previously seen could be constructed to be adjustable so as to permit eyewear member 655 to be mounted on various sizes of eyeglasses 523. This may be accomplishes as is shown for a single adjustable angled projection member 677 as seen.

Referring to FIG. 61, a section taken through line 61—61 of FIG. 60 illustrates a side view including a back wall 679 having a set of steps 681 under which the inner end of adjustable angled projection member 677 is adjusted to fit. A side slot 683 provides adjustable guidance for the adjustable angled projection member 677. Referring to FIG. 62, a section taken through line 62—62 of FIG. 61 illustrates a top view of the adjustable angled projection member 677 and further illustrates a set of shaped side pins 685 which project into the side slots 683. The width of the pins 685 enables the main extent of the adjustable angled projection member 677 to lie perpendicular with respect to the extent of the side slot 683 only at certain heights within the slot 683 where notches 687 are seen.

Referring to FIG. 63, an eyewear member 691 is seen as having a change in thickness with lesser depth of thickness nearer the inside, toward the nose position and thicker in depth as the eyewear member 691 extends nearer the outside position. In this manner a lifting, lifter, or space filling function is performed. The larger space between a user's face and the eyeglasses 523 occurs at the outermost extent away from the user's nose. The eyewear member 671 can have a main body which is wedge shaped and used in conjunction with a flat sealing member piece, or it can have a flat construction used in conjunction with a wedge shaped sealing member piece. In FIG. 63, a structural member 693 is shown with a wedge shaped length of sealing member 695.

Referring to FIG. 64, a view looking down upon a slightly different Eyewear member 697 illustrates a wedge shaped body 699 with a thin layer of sealing member 701.

Figure 65:
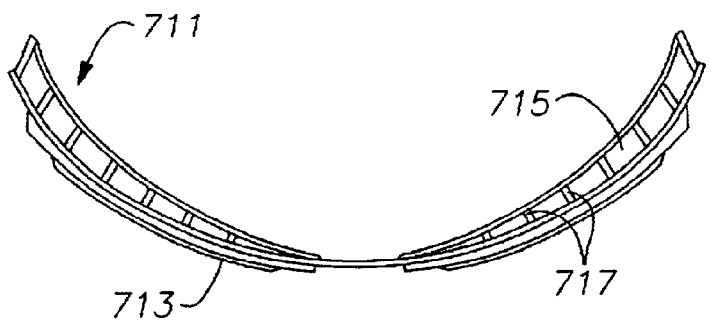
FIG. 65 is a top view looking down upon eyewear member and illustrating a detachable rear sealing member lifter.

Referring to FIG. 65, a top view looking down upon a further embodiment shown as eyewear member 711 shows the thin body 713, peripheral flange 543 and a rearwardly extending lifter 715 which may have a series of breather slots 717 for improved moisture removal. The lifters 715 help to "fill in" the space between the thin body 713 and the outside corner of the user's eye. When the further compression through normal fit of the eyeglasses 523 are added to the outer surface of the eyewear member 711, a snug seal against the users face will be enhanced by the lifters 715 which act to lift the closes surface to the user's face in a more snug fit to the user's face.

Figure 66:
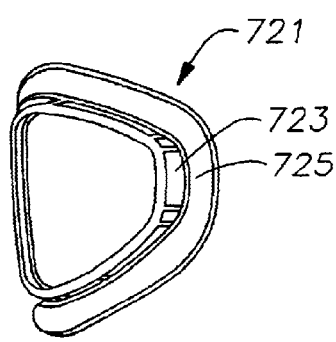
FIG. 66 is a side view of an embodiment of an eyewear member having an integral frontal lifter as integrated into a forward flange.

Referring to FIG. 66 is a side view of an embodiment of an eyewear member 721 having an integral frontal lifter as integrated into a forward flange 723. Eyewear member 721 is shown having the peripheral flange 543 having a differential height to form a forward or frontal lifter 723. The utilization of a lens, such as lens 530, can be had at any angle within the frontal lifter 723. Note that the frontal lifter 723 is raised farther from a main body 725 at one end of the eyewear member 721 than at the other.

Figure 67:
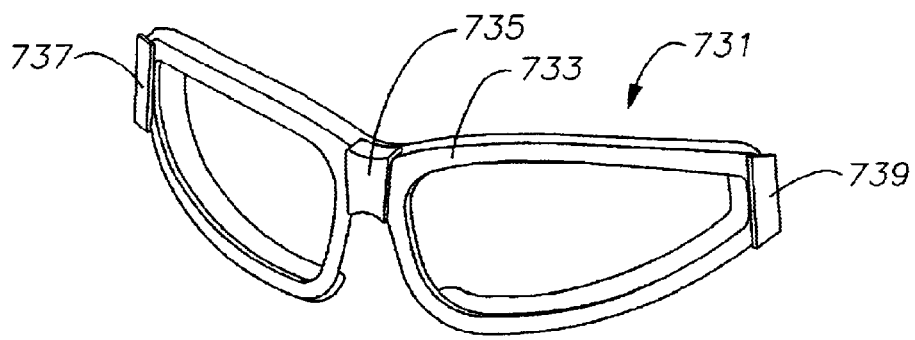
FIG. 67 is a perspective view illustrating peel off or break away front lifters which are mounted at the front temple and side openings of an eyewear member.

Referring to FIG. 67, a perspective view illustrating a frontal view of an eyewear member 731 illustrates a body 733 having a nose bridge lifter 735 and a pair of outwardly located lifters including a right side lifter 737 and a left side lifter 739. In the event that the user's head is not as narrow at the sides, lifters 737 and 739 can be peeled off or broken away. In the event that the user's head shape requires more clearance at the center of the eyewear member 731, the lifter 735 may be peeled away or broken away to give more clearance. In this manner, some fairly non-custom degree of fit can be selected by the user based upon head shape.

Figure 68:
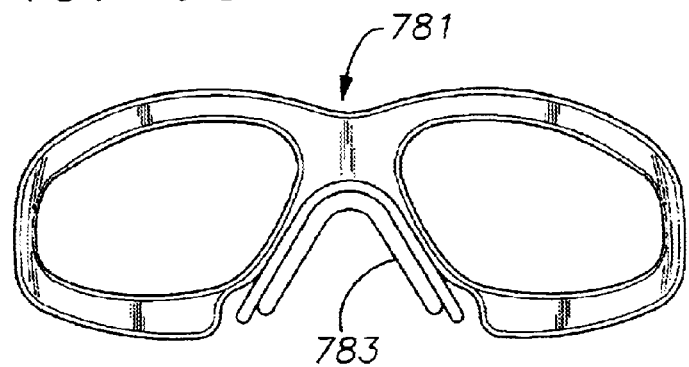
FIG. 68 is a rear view of an eyewear member having a nose piece integrally fitted and which may serve as the main nose piece especially in conjunction with eyewear not having a nosepiece or having a complementary shape, and shown with the removable seal members removed.

Referring to FIG. 68, a rear view of an eyewear member 781 illustrates the use of a nose piece 783 integrally fitted and which may serve as the main nose piece utilized especially in conjunction with eyewear not having a nose-piece or having a complementary shape. The nosepiece 783 has soft rearward projections which deflect as they engage the user's nose and provide both sealing and support to the users face at the area over the user's nose.

Figure 69:
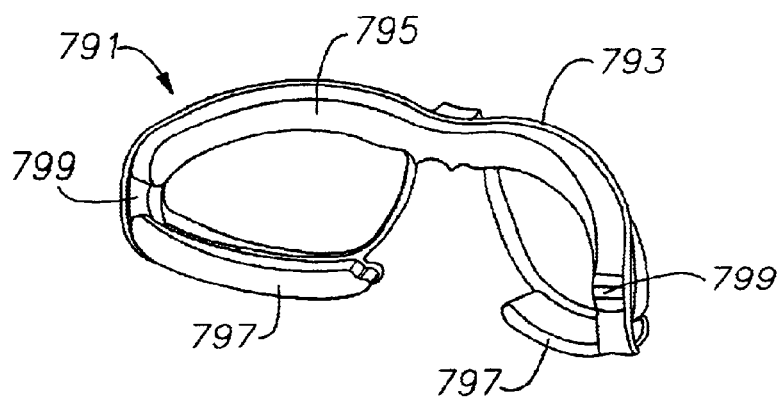
FIG. 69 is a rear view of an eyewear member showing the piecewise addition of sealing to customize the performance of the eyewear to create, for example, a slip stream of ventilation.

Referring to FIG. 69, a rear view of an eyewear member 791 reveals a body 793 having an upper seal 795 and a set of lower seals 797 which create an optional gap 799 between each of the lower seals 797 and the end of the upper seal 795. Such a gap 799 may be provided to enable controlled ventilation of sufficient magnitude that appreciable dust and debris does not enter the area around the user's eyes, but that adequate moisture removal occurs. The gap 799 can be adjusted smaller or larger to control ventilation as by cutting, or by simply fitting the seals 797 and 795 onto the body 793.

Figure 70:
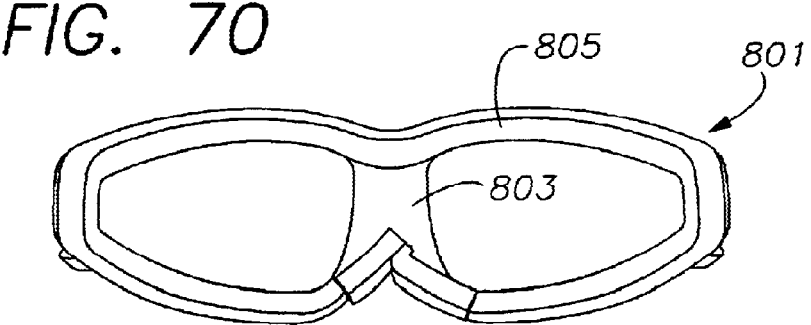
FIG. 70 illustrates a rear view of an eyewear member having a wide center member and in which a sealing member is placed to complete the seal.

Referring to FIG. 70, a rear view of an eyewear member 801 having a wide center member 803 and in which a seal 805 is placed completely around the body except for the wide center member 803, to form a complete seal for the eye areas, but not isolating one eye area from the other.

Referring to FIG. 71 a clam shell arrangement is seen, which may be physically connecting or magnetic, such as where a magnetic eyewear member 811 fits behind a conventional eyewear set 523 and, either by reach around or magnetic connection supports an decorative facade 813.

Decorative facade 813 may be available as a set of different colored interchangeable components or different styled components to enable a user to change color and look, even while keeping a single set of eyewear. Where expensive prescription lenses are utilized this feature can be of significant importance to enable different looks without having to spend on different multiple sets of lenses.

Referring to FIG. 72, a conventional sports eyewear glasses set 821 is shown with an eyewear member 823 which has an open clearing below the nose bridge to fit atop a conventional nosepiece 825 which is provided in the conventional eyewear 821. This system works well without angled projection members of any kind, and the need for angled projection members such as angled projection members 553, 555 or 551 may or may not be present, and where a angled projection member is needed, supplying one, two or all three of the angled projection members 551, 553, or 555 may be had. In some cases the angled projection members 551, 553, or 555 may be removable by the user where an eyewear member 521, 565, 573, 577, 581, 595, 607, 609, 613, 621, 641, 649, 655, 671, 691, 711, 721, 731, 781, 891, 801, 811, or 823 is provided with such removable physical attachment structures.

In addition, the front surface of the eyewear member 823 may have a high friction, highly deformable plastic coating or seal coating 825, especially like the types of surfaces used on lint rollers and the like, and which on a micro basis highly conforms to the surface features of the back of the conventional sports eyewear glasses set 821. This enables the user to "set" the relationship between the eyewear member 823 and the conventional sports eyewear glasses set 821 by simply pressing them together. Once set together, they may be worn nearly as a unitary piece. Removal is had by simply urging them directly apart. The seal coating 825, like the other removable seals herein, can be applied to the front of the eyewear member 825, and also to the rear of any eyemember, as has been shown in the drawings.

Figure 73:
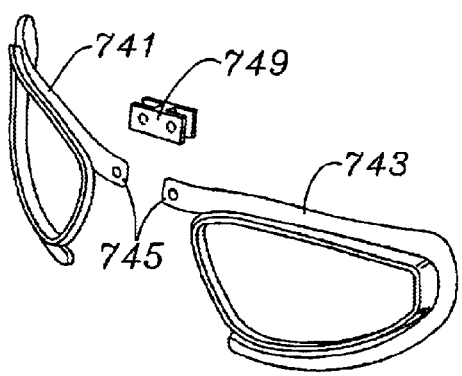
FIG. 73 illustrates a two piece eyewear member joinable by a center angular projection member which enables the two piece eyewear member to have some angular displacement and to be utilized separately, without the angular projection member.

Referring to FIG. 73, a set of two eyewear member portions 741 and 743 each have a side projection 745. A clip 747 has a center portion and a pair of end portions, each end portion having arms for engaging an associated one of the side projections 745 to form the two eyewear member portions 741 and 743 into a single two eyewear member set which may optionally have the ability to enable the two eyewear member portions 741 and 743 to achieve a variable angle with respect to each other to enable use with a wider variety of conventional eyewear.

Referring to FIG. 74, an enlarged view of an eyewear member 751 illustrates a series of three apertures 753 for interfitting with a removable angular projection member 755. Removable angular projection member 755 has an insertion portion 757 and an angular projection portion 759. By providing a set of three apertures 753, with each aperture 753 located a different distance from a visual aperture 781, the eyewear member 751 is made to fit with a wider array of conventional eyewear of different sizes. Also seen is a series of three apertures 783 for fitting an removable angular projection member (not shown) of a size and shape which would be similar to the member 551 of FIG. 43.

Referring to FIG. 75, a cross sectional view taken along line 75—75 of FIG. 74 illustrates the series of apertures 753, the middle one of which is occupied by the insertion of an insertion portion 757 of a removable angular projection member 755. The angular projection portion 759 is seen projecting upwardly and away from the front surface of the eyewear member 751.

The different embodiments of the eyewear member of this invention may be formed by being extruded or injection molded and then may be applied heat and then bent to have the eyewear member be altered in shape where it is desired. In the construction of any of the eyewear members of the present invention, there may be involved gluing, angled projection membering, clipping, chemical bonding, welding, friction fitting, screws, pressure, male and female pin arrangements and holes, attachment channel and groove, hook and loop fasteners, magnets, suction, static attraction, melting, solvents and independent attachment to other structures including any portion of the eyeglasses, temple earpieces, straps or lens. The eyewear member of the present invention may be formed homogeneously or can be constructed of two or more different types of material. Materials which can be used include wood, metal, plastic, leather, cloth/fabric, foam, rubber, conforming material and any other material capable of making the seal now known or later discovered manufacture of the eyewear members of the present invention can occur by extrusion, injection molding, shaping, forming, or any other type of molding. All of the cushioning foam members as well as the lifters structures may be designed to be removable in conjunction with the body structures of the eyewear members shown. The removing of each of the cushioning strips or foam strips may be for the purpose of utilizing different sizes of cushioning strips and possibly different shapes of cushioning strips. Further, structures may be covered with a tacky plastic layer in order to enhance adherence and sealing. This is especially true with plastics used for their tacky properties such are used to remove lint and dirt, but which wash free with soap and water.

The present invention may be used in any setting in which an expanded lens eyewear structure is desired to be fitted with a removable enclosing structure to give sealing protection similar to that for extremely restrictive eyewear, but in a structure which is more convenient and comfortable for the user, and which allows the user a choice of wearing mode. Multiple variations on this invention are certainly possible, since variations can occur with any one or any combination of the components of several of the fitted structures, sealing structures, lens interfitting structures described in the eyewear invention. Modifications to all parts of the invention may occur to those skilled in the art, and those modifications may be produced without departing from the spirit and scope of the invention. Therefore, included within the patent warranted hereon are all such changes and modifications as may reasonably and properly be included within the scope of this contribution to the art.

What is claimed:

1. A removable eyewear member for user selectable employment by a person wearing conventional eyewear, said eyewear member comprising:

a substantially planar, thin walled body utilizable with conventional eyewear, said body having an enclosure with at least one enlarged opening having a first lens, said enlarged opening to align with a second lens of said eyewear, said body to provide a close fit with a face of the person using said eyewear member to diminish the entry of foreign material and light between the eyewear and the person's face, said eyewear member having at least one projection for extending around conventional eyewear and attached to said eyewear member for mounting said eyewear member in juxtaposition to the conventional eyewear.

2. The eyewear member as defined in claim 1 wherein said body having mounted thereon mounting means for mounting of said eyewear member on a head of a user.

3. The eyewear member as defined in claim 2 wherein said mounting means comprises a strap.

4. The eyewear member as defined in claim 2 wherein said mounting means comprising temple earpieces.

* * * * *